(12) United States Patent
Chardes et al.

(10) Patent No.: US 9,127,065 B2
(45) Date of Patent: Sep. 8, 2015

(54) ANTI-HUMAN HER3 ANTIBODIES AND USES THEREOF

(75) Inventors: Thierry Chardes, Montpellier (FR);
Andre Pelegrin, Montpellier (FR);
Christel Larbouret, Montpellier (FR);
Nadege Gaborit, Rehovot (IL);
Yassamine Lazrek, Montpellier (FR)

(73) Assignees: Institut National de la Sante et de la Recherche Medicale (INSERM), Paris (FR); Centre Val d'Aurelle—Paul Lamarque, Montpellier Cedex (FR); Universite de Montpellier 1, Montpellier Cedex (FR)

( * ) Notice: Subject to any disclaimer, the term of this patent is extended or adjusted under 35 U.S.C. 154(b) by 0 days.

(21) Appl. No.: 14/118,747

(22) PCT Filed: May 21, 2012

(86) PCT No.: PCT/EP2012/059402
§ 371 (c)(1),
(2), (4) Date: Nov. 19, 2013

(87) PCT Pub. No.: WO2012/156532
PCT Pub. Date: Nov. 22, 2012

(65) Prior Publication Data
US 2014/0112931 A1    Apr. 24, 2014

Related U.S. Application Data

(60) Provisional application No. 61/499,948, filed on Jun. 22, 2011, provisional application No. 61/507,932, filed on Jul. 14, 2011.

(30) Foreign Application Priority Data

May 19, 2011    (EP) .................................... 11305607

(51) Int. Cl.
*A61K 39/395*    (2006.01)
*C07K 16/28*    (2006.01)
*C07K 16/32*    (2006.01)

(52) U.S. Cl.
CPC ............. *C07K 16/2863* (2013.01); *C07K 16/32* (2013.01); *C07K 2317/34* (2013.01); *C07K 2317/76* (2013.01); *C07K 2317/77* (2013.01); *C07K 2317/92* (2013.01)

(58) Field of Classification Search
None
See application file for complete search history.

(56) References Cited

FOREIGN PATENT DOCUMENTS

| WO | 2007/077028 A2 | 7/2007 |
| WO | 2008/100624 A2 | 8/2008 |
| WO | 2010/127181 A1 | 11/2010 |

OTHER PUBLICATIONS

Strome et al., The Oncologist, 2007; 12:1084-95.*
Brand et al., Anticancer Res. 2006; 26:463-70.*
Kani et al., "The extracellular domains of Erb3 retain high ligand binding affinity at endosome pH and in the locked conformation", Biochemistry, Dec. 2005, pp. 15842-15857, vol. 44, No. 48.

* cited by examiner

*Primary Examiner* — Sheela J Huff
(74) *Attorney, Agent, or Firm* — Whitham Curtis Chistofferson & Cook, PC

(57) ABSTRACT

The present invention provides for isolated anti-human-HER3 antibodies or fragments thereof. More particularly the present invention provides an isolated monoclonal antibody that specifically binds to the extracellular domain of HER-3 and competes for binding to the extracellular domain of human HER-3 with the antibody produced obtainable from hybridoma deposited as CNCM-I-4486. The antibodies described in the present invention are useful for the treatment of cancer.

13 Claims, 21 Drawing Sheets

| Hybridoma | Ascite formation | Ab ascite titer * | Purified Ab (mg/ml) | Ab titer after purification * |
|---|---|---|---|---|
| 15D4-F2 | +++ | 10 M | 0.20 | 300 pg/ml |
| 12H8-B11 | +++ | 1 M | 3.50 | 30 ng/ml |
| 14H1-H8 | + | 1000 | 0.18 | 250 µg/ml |
| 11G10-D2 | (+) | 3 M | 0.57 | 50 µg/ml |
| 4H9-D11 | +++ | 100 | 0.10 | 350 ng/ml |
| 16D3-C1 | ++ | 3 M | 1.20 | 150 pg/ml |
| 9B4-D6 | (+) | 10000 | 0.05 | 1 µg/ml |
| 9F7-F11 | ++ | 5 M | 3.50 | 400 pg/ml |
| 23H2-B3 | +++ | 1 M | 9.40 | 1 ng/ml |
| 24E3-C10 | +++ | 10000 | 0.16 | 40 ng/ml |

* Antibody dilution or Ab concentration showing an absorbance of 1 by ELISA towards a 250 ng/ml coating solution of HER3 receptor

Figure 2B

| Antibody | Wt 3T3 cells | Transfected 3T3 cells | | | | |
|---|---|---|---|---|---|---|
| | | EGFR | HER2 | HER3 | HER2/HER3 | EGFR/HER |
| Anti-mouse 2nd Ab | 0.3 | 0.4 | 0.4 | 0.3 | 0.3 | 0 |
| Control Px | 0.5 | 0.3 | 0.6 | 0.4 | 0.5 | 0 |
| 4H9-D11 | 0.3 | 0.3 | 0.3 | 0.7 | 1.3 | r |
| 9B4-D6 | 0.2 | 0.2 | 0.3 | 6.6 | 18.3 | r |
| 9F7-F11 | 0.3 | 0.4 | 0.4 | 1.8 | 12.4 | 0 |
| 11G10-D2 | 0.3 | 0.2 | 0.3 | 1.4 | 10.1 | r |
| 12H8-B11 | 0.3 | 0.4 | 0.5 | 3.7 | 28.8 | 0 |
| 14H1-H8 | 0.4 | 0.4 | 0.5 | 0.9 | 1.1 | r |
| 15D4-F2 | 0.4 | 0.3 | 0.4 | 4.2 | 25.6 | r |
| 16D3-C1 | 0.4 | 0.4 | 0.7 | 4.5 | 26.8 | 0 |
| U1-59 | 0.4 | 0.2 | 0.4 | 9.3 | 15.5 | 0 |
| Ab6 | 0.4 | 0.2 | 0.3 | 7.8 | 14.1 | 0 |

* Geometric mean

Figure 3

| Cell line | Control | Px | Trastuzumab | Anti-HER3 Antibody | | |
|---|---|---|---|---|---|---|
| | | | | 16D3-C1 | 12H8-B11 | 9F7-F11 |
| HER2/HER3 transfected fibroblasts H2P3 | 4.3 ± 0.8[a] | 17.8 ± 1.6 | 23.7 ± 5.9 | 1.8 ± 5.5 | 32.0 ± 9.0 | |
| Pancreatic cancer | | | | | | |
| HER3+ HPAC | < 0.0 | < 0.0 | < 0.0 | nd[b] | 7.0 | |
| HER3+ CFPAC | < 0.0 | < 0.0 | 2.3 | nd | 4.5 | |
| HER3+ BxPC3 | < 0.0 | 0.9 | < 0.0 | nd | 5.8 | |
| HER3- Capan | < 0.0 | < 0.0 | < 0.0 | nd | 0.7 | |
| Breast cancer | | | | | | |
| HER3+ MCF7 | 0.0 | 16.2 | 22.6 | nd | 32.7 | |
| HER3+ MDA-MB361 | < 0.0 | 21.3 | 9.0 | nd | 16.3 | |
| HER3+ T47D | < 0.0 | 14.8 | < 0.0 | nd | 14.4 | |
| HER3- MDA-MB231 | < 0.0 | < 0.0 | 2.5 | nd | 5.0 | |
| HER3+ epidermoid carcinoma A431 | < 0.0 | 3.4 | 7.7 | nd | 16.1 | |
| Ovarian cancer | | | | | | |
| HER3+ COV434-AMHR-II (granulosa) | < 0.0 | 3.2 | 6.3 | < 0.0 | 9.6 | |
| HER3+ ascite 1 clone A5 (epithelial) | 2.4 | 0.4 | 19.0 | 26.0 | 8.9 | |
| HER3+ ascite 2 clone C9 (epithelial) | 0.3 | < 0.0 | 15.3 | 5.2 | 12.6 | |
| Meta 2815 (epithelial) | 0.2 | < 0.0 | 15.3 | 2.1 | 6.1 | |
| HER3+ OVCAR3 (epithelial) | 2.2 | 7.4 | 6.5 | 6.0 | 7.0 | |
| HER3low SKOV3 (epithelial) | 0.3 | 5.4 | 4.6 | 1.1 | 6.6 | |
| HER3+ A549 lung carcinoma (NSCLC) | 5.6 | 4.5 | 2.7 | 2.6 | 9.8 | |

[a] Growth inhibition (%)
[b] nd: not done

Figure 11

A
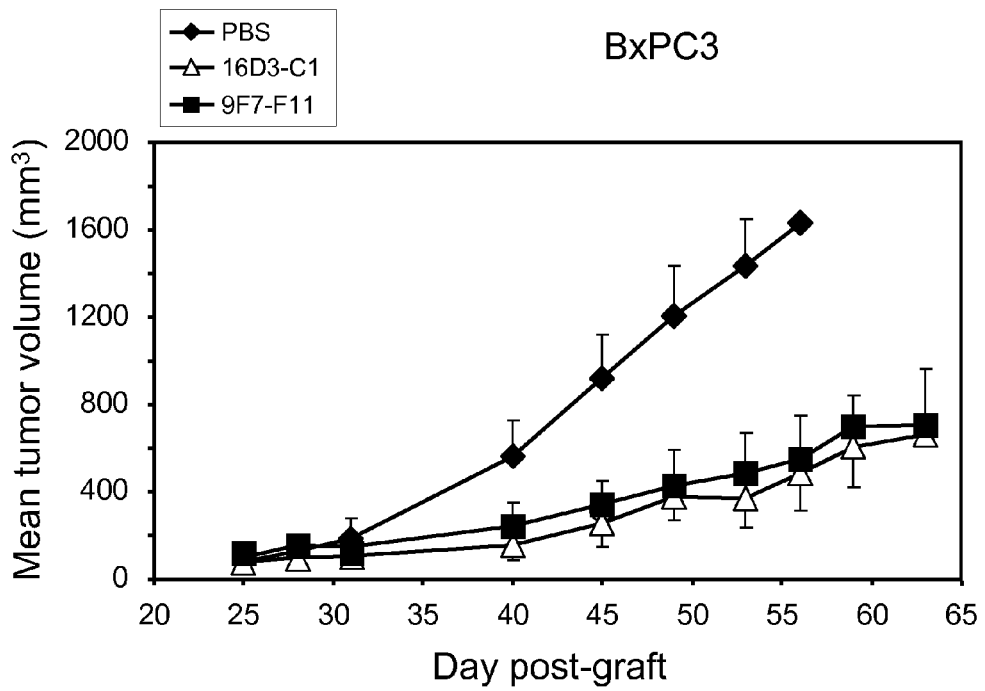
B
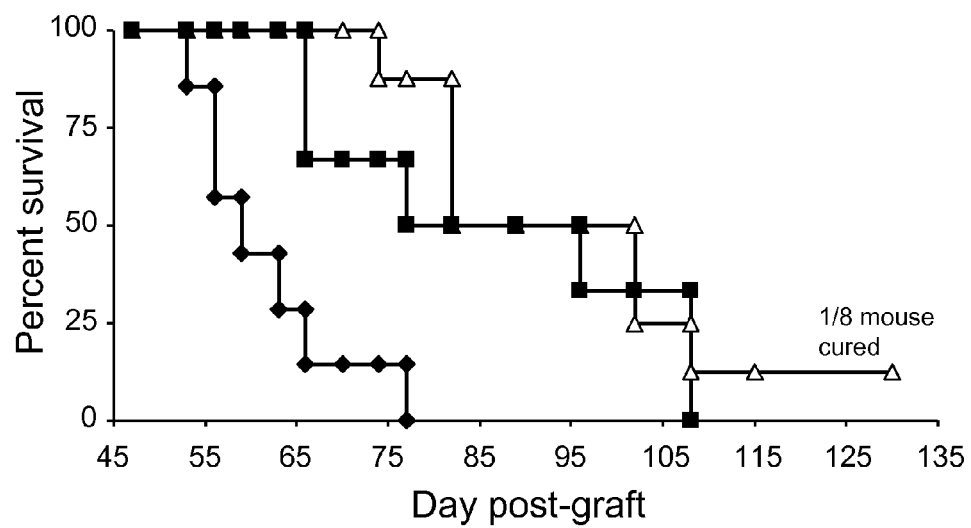
Figure 17

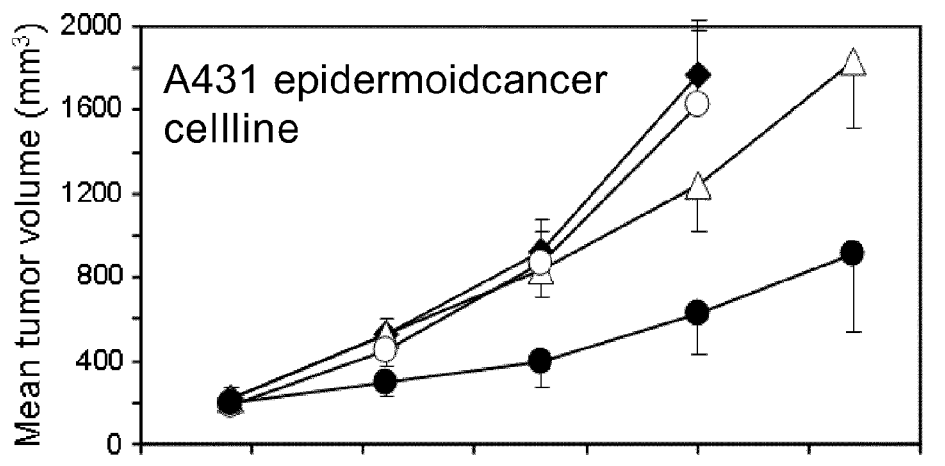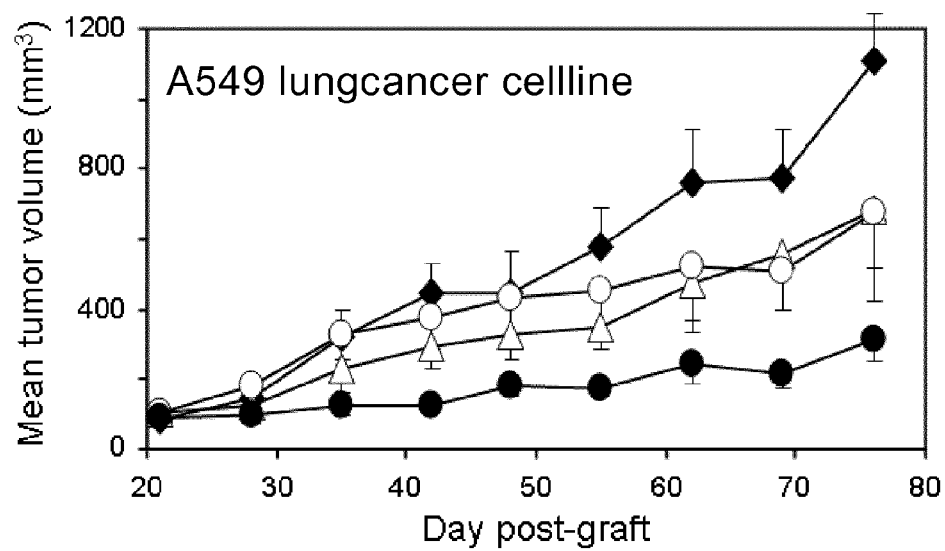
Figure 19

SEQUENCE LISTING

<160> NUMBER OF SEQ ID NOS: 16

<210> SEQ ID NO 1
<211> LENGTH: 15
<212> TYPE: PRT
<213> ORGANISM: Artificial Sequence
<220> FEATURE:
<223> OTHER INFORMATION: peptide

<400> SEQUENCE: 1

Ala Leu Arg Gln Leu Arg Leu Thr Gln Leu Thr Glu Ile Leu Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Peptide

<400> SEQUENCE: 2

Leu Arg Gln Leu Arg Leu Thr Gln Leu Thr Glu Ile Leu Ser Gly
1               5                   10                  15

```
<210> SEQ ID NO 3
<211> LENGTH: 15
<212> TYPE: PRT
<213> ORGANISM: Artificial Sequence
<220> FEATURE:
<223> OTHER INFORMATION: Peptide

<400> SEQUENCE: 3

Arg Gln Leu Arg Leu Thr Gln Leu Thr Glu Ile Leu Ser Gly Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Peptide

<400> SEQUENCE: 4

Arg Gln Leu Arg Leu Thr Gln Leu Thr Glu Ile Leu Ser Gly Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Peptide

<400> SEQUENCE: 5

Gln Leu Arg Leu Thr Gln Leu Thr Glu Ile Leu Ser Gly Gly Val
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Peptide

<400> SEQUENCE: 6

Leu Arg Leu Thr Gln Leu Thr Glu Ile Leu Ser Gly Gly Val Tyr
1               5                   10                  15

<210> SEQ ID NO 7
<211> LENGTH: 5
<212> TYPE: PRT
<213> ORGANISM: Artificial Sequence
<220> FEATURE:
<223> OTHER INFORMATION: Peptide

<400> SEQUENCE: 7

Leu Glu Ile Val Leu
1               5

<210> SEQ ID NO 8
<211> LENGTH: 15
<212> TYPE: PRT
<213> ORGANISM: Artificial Sequence
<220> FEATURE:
<223> OTHER INFORMATION: Peptide

<400> SEQUENCE: 8

Tyr Glu Arg Cys Glu Val Val Met Gly Asn Leu Glu Ile Val Leu
1               5                   10                  15
```

```
-continued

<210> SEQ ID NO 9
<211> LENGTH: 15
<212> TYPE: PRT
<213> ORGANISM: Artificial Sequence
<220> FEATURE:
<223> OTHER INFORMATION: Peptide

<400> SEQUENCE: 9

Glu Arg Cys Glu Val Val Met Gly Asn Leu Glu Ile Val Leu Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Peptide

<400> SEQUENCE: 10

Arg Cys Glu Val Val Met Gly Asn Leu Glu Ile Val Leu Thr Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Peptide

<400> SEQUENCE: 11

Cys Glu Val Val Met Gly Asn Leu Glu Ile Val Leu Thr Gly His
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Peptide

<400> SEQUENCE: 12

Glu Val Val Met Gly Asn Leu Glu Ile Val Leu Thr Gly His Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Peptide

<400> SEQUENCE: 13

Val Val Met Gly Asn Leu Glu Ile Val Leu Thr Gly His Asn Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Peptide

<400> SEQUENCE: 14

Val Met Gly Asn Leu Glu Ile Val Leu Thr Gly His Asn Ala Asp
1               5                   10                  15
```

```
<210> SEQ ID NO 15
<211> LENGTH: 15
<212> TYPE: PRT
<213> ORGANISM: Artificial Sequence
<220> FEATURE:
<223> OTHER INFORMATION: Peptide

<400> SEQUENCE: 15

His Ala Leu Arg Gln Leu Arg Leu Thr Gln Leu Thr Glu Ile Leu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Peptide

<400> SEQUENCE: 16

Arg Leu Thr Gln Leu Thr Glu Ile Leu Ser Gly Gly Val Tyr Ile
1               5                   10                  15
```

ANTI-HUMAN HER3 ANTIBODIES AND USES THEREOF

FIELD OF THE INVENTION

The present invention relates to anti-human-HER3 antibodies and uses thereof in diagnostic and therapeutic methods.

BACKGROUND OF THE INVENTION

The human epidermal growth factor receptor ErbB/HER family of receptor tyrosine kinases (RTK) includes four members: EGFR (ErbB1/HER1), HER2 (c-Neu, HER2), HER3 (HER3) and HER4 (HER4). The HER receptors comprise an extracellular glycosylated domain consisting of four structural domains, marked 1 to 4, followed by a transmembrane domain and an intracellular C-terminal part containing a kinase domain for coupling to signalling pathways. Except for HER3, the intracellular region contains a tyrosine kinase activity. Signalling is mediated through ligand-induced receptor dimerization and subsequent phosphorylation that leads to the activation of cytoplasmic signalling pathways. HER2 has no specific ligand because it is naturally under an "active" conformation. The other HER receptors exist as inactive monomers with the molecules folded in such a way to prevent dimerization. Ligand binding to domains 1 and 3 induces major conformational changes ultimately exposing the dimerization loop in domain 2 of the receptor. This exposure of the dimerization loop allows for receptor dimerization.

The HER3 receptor, that has been first described in 1990, is the only HER family member receptor that lacks the intrinsic kinase activity and downstream signalling is achieved through heterodimerization. Thus, the HER3 receptor, as a monomer, is called "non-self" and cannot form homodimers. Binding of the ligand Heregulin (HRG) to HER3 receptor triggers the heterodimerization of HER3 with the others HER family receptors (HER2 preferentially). Within the heterodimer, the HER3 kinase domain acts as an allosteric activator of its HER family partner.

HER3 is implicated in tumorigenesis of various cancers including breast and ovarian cancer (Lee-Hoeflich S T, Cancer Res. 2008; McIntyre E, Breast Cancer Res Treat. 2010; Tanner B, J Clin Oncol. 2006). HER3 expression correlates with tumor progression and reduced patient survival in malignant melanoma and metastases, and is associated with decrease survival in ovary cancer. Importantly, in breast cancer, tumors with low HER2 expression, which are not eligible to Herceptin treatment, often are "programmed" to strongly express HER3 (Smith et al. Br. J. Cancer 2004), and HER2+++ tumors, which become resistant to Herceptin after prolonged treatment, are "re-programmed" to strongly express HER3 (Narayan, Cancer Res. 2009). Cetuximab resistance was also associated with HER3 over-expression in lung cancer (Wheeler, Oncogene 2008) and colorectal carcinomas (Lu Cancer Res 2007), together with dysregulation of EGFR internalization/degradation. Recently, HER3 over-expression was significantly associated with worse metastasis-free survival in colorectal carcinoma (Ho-Pun-Cheung, Int J Cancer 2010). Thus, HER3 over-expression and compensatory signalling through activation of the PI3K/AKT pathway are implicated in the development of resistance to treatment with HER-targeted therapies (antibodies and TKI) (Wheeeler 2008, Lu 2007, Narayan, 2009, Sergina, 2007) but also to treatment with IGFR-targeted therapies (Desbois-Mouthon, Clin Cancer Res 2009) and with chemotherapeutic agents (Kruser, Exp Cell Res 2010).

All these findings suggest that HER3-targeted agents, and in particular antibodies, might help to further understand the role of HER3 signalling in cancers and especially be used as efficient immunotherapeutics.

At present, no therapeutic anti-HER3 antibody is commercialized although the scientific literature strongly emphasizes the interest of targeting HER3 in therapeutic oncology. Two human antibodies are currently under development by Merrimack Pharmaceuticals/Sanofi Aventis (MM-121 antibody; PCT WO2008/100624) and U3 PharmaAG/Daiichi Sankyo/Amgen (U3-1287 or AMG-888; PCT WO2007/077028). MM-121 antibody is involved in a phase I clinical trial in NSCLC and in a phase I/II trial in ER+PR+ HER2− breast cancer. U3-1287 antibody is in phase I in NSCLC in association with Erlotinib. One EGFR/HER3 bispecific antibody DL11f (Genentech; PCT WO2010/108127) is still in research development. One HER2/HER3 bispecific antibody MM-111 (Merrimack Pharmaceuticals; PCT WO2005/117973, WO2006/091209) is involved in phase I/II clinical trials, alone or in combination with trastuzumab or lapatinib, in HER2-amplified breast cancer.

All the above mentioned antibodies block the heregulin-binding site of the HER3 receptor, thus reducing these antibody therapies to ligand-addicted tumors. Targeting HER3 with antibodies that are not directed to the heregulin-binding site of HER3 should make possible to bypass the resistance to targeted therapies or chemotherapy in resistant HER2-amplified breast cancer, to broaden the application field of targeted therapies to HER2low breast cancer, which are currently not eligible for such treatment, or to treat triple-negative breast cancers, which express HER3 and for which no targeted therapy is available yet.

SUMMARY OF THE INVENTION

The present invention provides for isolated anti-human-HER3 antibodies or fragments thereof.

An aspect of the present invention provides an isolated monoclonal antibody that specifically binds to the extracellular domain of HER-3 and competes for binding to the extracellular domain of human HER-3 with the antibody produced obtainable from hybridoma deposited as CNCM-I-4486.

A further aspect of the invention relates to a monoclonal antibody comprising a variable light chain (VL) comprising the CDRs of the VL chain of the antibody obtainable from hybridoma deposited as CNCM-I-4486 and a variable heavy chain (VH) comprising the CDRs of the VH chain of the antibody obtainable from hybridoma deposited as CNCM-I-4486.

A further aspect of the invention relates to a monoclonal antibody comprising the VL chain of the antibody obtainable from hybridoma deposited as CNCM-I-4486 and the VH chain of the antibody obtainable from hybridoma deposited as CNCM-I-4486.

A further aspect of the invention relates to a monoclonal chimeric antibody, which comprises the variable domains of the antibody obtainable from hybridoma deposited as CNCM-I-4486.

A further aspect of the invention relates to a monoclonal humanized antibody comprising the CDRs of the antibody obtainable from hybridoma deposited as CNCM-I-4486.

A further aspect of the invention thus relates to a murine monoclonal antibody (16D3-C1) obtainable from the hybridoma available under CNCM deposit number I-4486.

The invention also further provides antibody fragments of said antibodies which include but are not limited to Fv, Fab, F(ab')2, Fab', dsFv, scFv, sc(Fv)2 and diabodies.

DETAILED DESCRIPTION OF THE INVENTION

The inventors have characterized a murine anti-human-HER3 antibody. In particular the inventors have deposited a murine anti-human-HER3 antibody (16D3-C1) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on May 17, 2011. The deposited hybridoma has CNCM deposit number I-4486. The inventors have, in particular shown that this antibody is a potent inhibitor of the formation of the heterodimer HER2-HER3 complex, and that inhibition was independent on ligand heregulin.

DEFINITIONS

The term "HER3" refers to the human HER3 receptor as described in Plowman et al., Proc. Natl. Acad. Sci. USA, 87:4905-4909 (1990); see, also, Kani et al., Biochemistry 44: 15842-857 (2005), Cho and Leahy, Science 297: 1330-1333 (2002). HER3 is also known as "HER3".

The term "anti-human-HER3 antibody" refers to an antibody directed against human HER3.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody derived the 16D3-C1 antibody, and a CH domain and a CL domain of a human antibody.

According to the invention, the term "humanized antibody" refers to an antibody having variable region framework and constant regions from a human antibody but retains the CDRs of the 16D3-C1 antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

Antibodies of the Invention:

The present invention provides for isolated anti-human-HER3 antibodies or fragments thereof. In particular, the inventors have deposited a murine anti-human-HER3 antibody (16D3-C1) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on May 17, 2011. The deposited hybridoma has CNCM deposit number I-4486.

An aspect of the present invention provides an isolated monoclonal antibody that specifically binds to the extracellular domain of HER-3 and competes for binding to the extracellular domain of human HER-3 with the antibody produced obtainable from hybridoma deposited as CNCM-I-4486.

In a particular embodiment, said antibody is selected from the group consisting of a murine antibody, a chimeric antibody, a humanized antibody, and a human antibody A further aspect of the invention relates to a monoclonal antibody comprising a variable light chain (VL) comprising the CDRs of the VL chain of the antibody obtainable from hybridoma deposited as CNCM-I-4486 and a variable heavy chain (VH) comprising the CDRs of the VH chain of the antibody obtainable from hybridoma deposited as CNCM-I-4486.

A further aspect of the invention relates to a monoclonal antibody comprising the VL chain of the antibody obtainable from hybridoma deposited as CNCM-I-4486 and the VH chain of the antibody obtainable from hybridoma deposited as CNCM-I-4486.

A further aspect of the invention relates to a monoclonal chimeric antibody, which comprises the variable domains of the antibody obtainable from hybridoma deposited as CNCM-I-4486.

A further aspect of the invention relates to a monoclonal humanized antibody comprising the CDRs of the antibody obtainable from hybridoma deposited as CNCM-I-4486.

A further aspect of the invention thus relates to a murine monoclonal antibody (16D3-C1) obtainable from the hybridoma available under CNCM deposit number I-4486.

The invention also further provides antibody fragments of said antibodies which include but are not limited to Fv, Fab, F(ab')2, Fab', dsFv, scFv, sc(Fv)2 and diabodies.

Competitive Binding Assays:

The present invention thus relates to pan isolated monoclonal antibody that specifically binds to the extracellular domain of HER-3 and competes for binding to the extracellular domain of human HER-3 with the antibody produced obtainable from hybridoma deposited as CNCM-I-448.

Epitope binning can be used to identify antibodies that fall within the scope of the claimed invention. Epitope binning refers to the use of competitive binding assays to identity pairs of antibodies that are, or are not, capable of binding HER3 simultaneously, thereby identifying pairs of antibodies that bind to the same or overlapping epitopes on HER3. Epitope binning experiments provide evidence that antigenically distinct epitopes are present. Competition for binding can be evaluated for any pair of antibodies or fragments. For example, using the appropriate detection reagents, the binding specificity of antibodies or binding fragments from any source can be compared to the binding specificity of the monoclonal antibodies disclosed herein. Epitope binning can be performed with "isolated antibodies" or with cell culture supernatants. Frequently, binning is performed with first round clonal supernatants to guide the choice of clones to be developed further. The antibodies to be compared should be substantially homogeneous antigen binding domains. In the case of "bispecific" or "bifunctional" antibodies the binding specificity of the two different binding sites need to be evaluated or binned independently.

The antibodies of the present invention may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Methods of Producing Antibodies of the Invention:

Anti-human-HER3 antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid sequence encoding an antibody according to the invention.

In a particular embodiment, the invention relates to a nucleic acid sequence encoding the VH domain of the antibody of the invention (e.g. the antibody obtainable from hybridoma deposited as CNCM-I-4486 (16D3-C1)) or the VL domain of the antibody of the invention (e.g. the antibody obtainable from hybridoma deposited as CNCM-I-4486 (16D3-C1)).

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3×63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

In another particular embodiment, the method comprises the steps of:

(i) culturing the hybridoma deposited as CNCM-I-4486 under conditions suitable to allow expression of 16D3-C1 antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan EA (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human HER3 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with human HER3 with a protease, pepsin. Also, the F(ab')2 can be produced by binding Fab' described below via a thioether bond or a disulfide bond.

The Fab' of the present invention can be obtained treating F(ab')2 which specifically reacts with human HER3 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. No. 4,640,835; 4,496, 689; 4,301, 144; 4,670, 417; 4,791, 192 or 4,179,337.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992)

Immunoconjugates:

An antibody of the invention can be conjugated with a detectable label to form an anti-HER3 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-HER3 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-HER3 immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-HER3 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-HER3 immunoconjugates can be detectably labeled by linking an anti-human-HER3 monoclonal antibody to an enzyme. When the anti-HER3-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-human-HER3 monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-human-HER3 monoclonal antibodies that have been conjugated with avidin, streptavidin, and biotin. (See, e.g., Wilchek et al. (eds.), "Avidin-Biotin Technology," *Methods In Enzymology* (*Vol.* 184) (Academic Press 1990); Bayer et al., "Immunochemical Applications of Avidin-Biotin Technology," in

*Methods In Molecular Biology (Vol.* 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

In another aspect, the present invention provides an anti-human-HER3 monoclonal antibody-drug conjugate. An "anti-human-HER3 monoclonal antibody-drug conjugate" as used herein refers to an anti-human-HER3 monoclonal antibody according to the invention conjugated to a therapeutic agent. Such anti-human-HER3 monoclonal antibody-drug conjugates produce clinically beneficial effects on HER3-expressing cells when administered to a subject, such as, for example, a subject with a HER3-expressing cancer, typically when administered alone but also in combination with other therapeutic agents.

In typical embodiments, an anti-human-HER3 monoclonal antibody is conjugated to a cytotoxic agent, such that the resulting antibody-drug conjugate exerts a cytotoxic or cytostatic effect on a HER3-expressing cell (e.g., a HER3-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-human-HER3 monoclonal antibody can be conjugated to a cytotoxic agent such as a chemotherapeutic agent or a toxin (e.g., a cytostatic or cytocidal agent such as, for example, abrin, ricin A, pseudomonas exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etoposide phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-HER3-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-human-HER3 monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

Diagnostic Uses:

A further object of the invention relates to an anti-human-HER3 antibody of the invention for diagnosing and/or monitoring a cancer disease associated with HER3 expression. Cancer diseases associated with HER3 expression typically include but are not limited to squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer diagnosed using the methods of the present invention is breast cancer or ovarian cancer. In a preferred embodiment, antibodies of the invention are useful for diagnosing breast and ovarian cancer.

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, mri), such as iodine-123, iodine-131, indium-I11, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for staging of cancer diseases associated with HER3 expression (e.g., in radioimaging). For example, antibodies of the invention may be useful for staging a breast or ovarian cancer. They may be used alone or in combination with other breast or ovarian cancer markers, including, but not limited to, HER2, CAl 25, HE4 and mesothelin.

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with HER3 expression, and in a preferred embodiment from breast or ovary. Therefore, biological samples encompass clinical samples, cells in culture, cell supernatants, cell lysates, serum, plasma, biological fluid, and tissue samples.

In a particular embodiment, the invention is a method of diagnosing a cancer disease associated with HER3 expression in a subject by detecting HER3 on cells from the subject using the antibody of the invention. In particular, said method of diagnosing may comprise the steps consisting of:

(a) contacting a biological sample of a subject likely to suffer from a cancer disease associated with HER3 expression with an antibody according to the invention in conditions sufficient for the antibody to form complexes with cells of the biological sample that express HER3;

(b) detecting and/or quantifying said complexes, whereby the detection of said complexes is indicative of a cancer disease associated with HER3 expression.

In order to monitor the cancer disease, the method of diagnosing according to the invention may be repeated at different intervals of time, in order to determine if antibody binding to the samples increases or decreases, whereby it is determined if the cancer disease progresses or regresses.

Therapeutic Uses:

Antibodies, fragments or immunoconjugates of the invention may be useful for treating any HER3-expressing cancer. The antibodies of the invention may be used alone or in combination with any suitable agent.

Examples of HER3-expressing cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated using the methods of the present invention is breast cancer or ovarian cancer.

Thus, an object of the invention relates to a method for treating a cancer associated with the expression of HER3 comprising administering a subject in need thereof with a therapeutically effective amount of an antibody, fragment or immunoconjugate of the invention.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof" is intended for a human or non-human mammal affected or likely to be affected with cancer associated with the expression of human HER3 cancer associated with the expression of human HER3.

By a "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

In certain embodiments, an anti-human-HER3 monoclonal antibody or antibody-drug conjugate is used in combination with a second agent for treatment of a disease or disorder. When used for treating cancer, an anti-human-HER3 monoclonal antibody or antibody-drug conjugate of the present invention may be used in combination with conventional cancer therapies such as, e.g., surgery, radiotherapy, chemotherapy, or combinations thereof. In certain aspects, other therapeutic agents useful for combination cancer therapy with an anti-HER3 antibody or antibody-drug conjugate in accordance with the present invention include anti-angiogenic agents. In some aspects, an antibody or antibody-drug conjugate in accordance with the present invention is co-administered with a cytokine (e.g., a cytokine that stimulates an immune response against a tumor.

In some other aspects, other therapeutic agents useful for combination therapy include an antagonist of certain factors that are involved in tumor growth such as, for example, EGFR, HER2, or HER4.

In a preferred embodiment an anti-human-HER3 monoclonal antibody or antibody-drug conjugate of the present invention is used in combination with an anti-human-HER2 monocolonal antibody, such as Trastuzumab or Pertuzumab.

In some embodiments, an anti-human-HER3 monoclonal antibody or antibody-drug conjugate as described herein is used in combination with a tyrosine kinase inhibitor (TKI). BAY 43-9006 (sorafenib, Nexavar®) and SU11248 (sunitinib, Sutent®) are two such TKIs that have been approved. Other TKIs include, but are not limited to: Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (Array BioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Midostaurin (Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

Pharmaceutical Compositions:

For administration, the anti-human-HER3 monoclonal antibody or antibody-drug conjugate is formulated as a pharmaceutical composition. A pharmaceutical composition comprising an anti-human-HER3 monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995).) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits:

Finally, the invention also provides kits comprising at least one antibody of the invention. Kits containing antibodies of the invention find use in detecting HER3 expression, or in therapeutic or diagnostic assays. Kits of the invention can contain an antibody coupled to a solid support, e.g., a tissue culture plate or beads (e.g., sepharose beads). Kits can be provided which contain antibodies for detection and quantification of HER3 in vitro, e.g. in an ELISA or a Western blot. Such antibody useful for detection may be provided with a label such as a fluorescent or radiolabel.

The invention will be further illustrated by the following figures and examples. However, these examples and figures should not be interpreted in any way as limiting the scope of the present invention.

FIGURES

FIG. 3 show flow cytometry specific binding profile (geometric mean) of purified mouse IgG 4H9-B11, 9B4-D6, 9F7-F11, 11G10-D2, 12H8-B11, 14H1-H8, 15D4-F2 and 16D3-C1 to wt-, EGFR-, HER2-, HER3-, HER2/HER3- and EGFR/HER4-transfected NIH 3T3 cells. Px antibody is a negative control. Competitor antibodies Ab6 and U1-59 are indicated.

Figure 4:
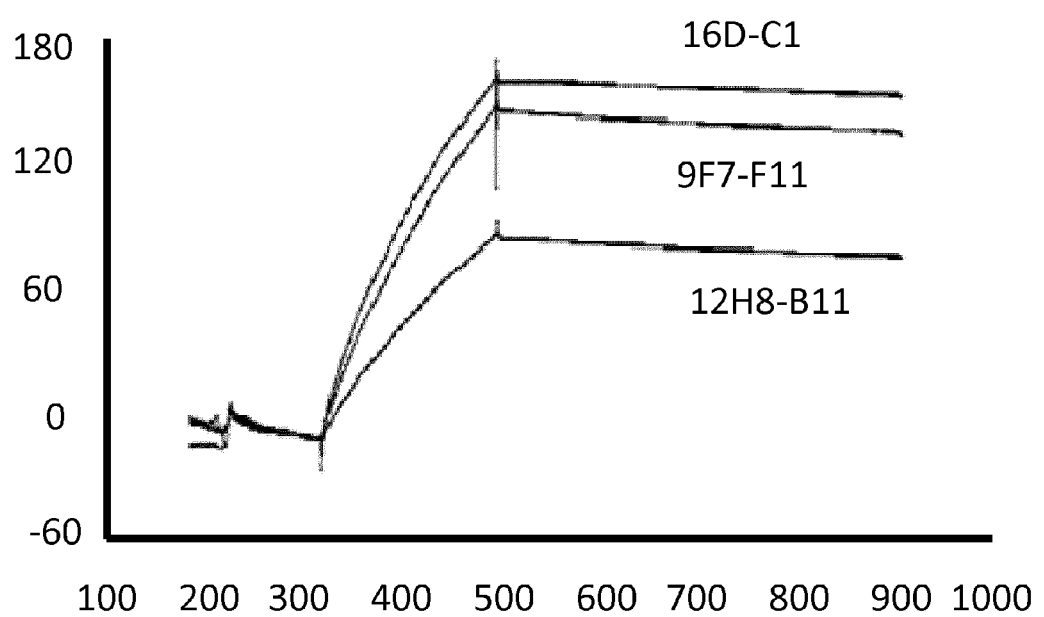

FIG. 4 shows the BIACORE binding kinetics of mAbs 16D3-C1, 9F7-F11 and 12H8-B11. Table 6 shows the affinity of the purified mouse antibodies 9F7-F11, 11G10-D2, 12H8-B11, 14H1-H8, 15D4-F2 and 16D3-C1 of the invention with regard to Ab6 antibody.

Figure 5:
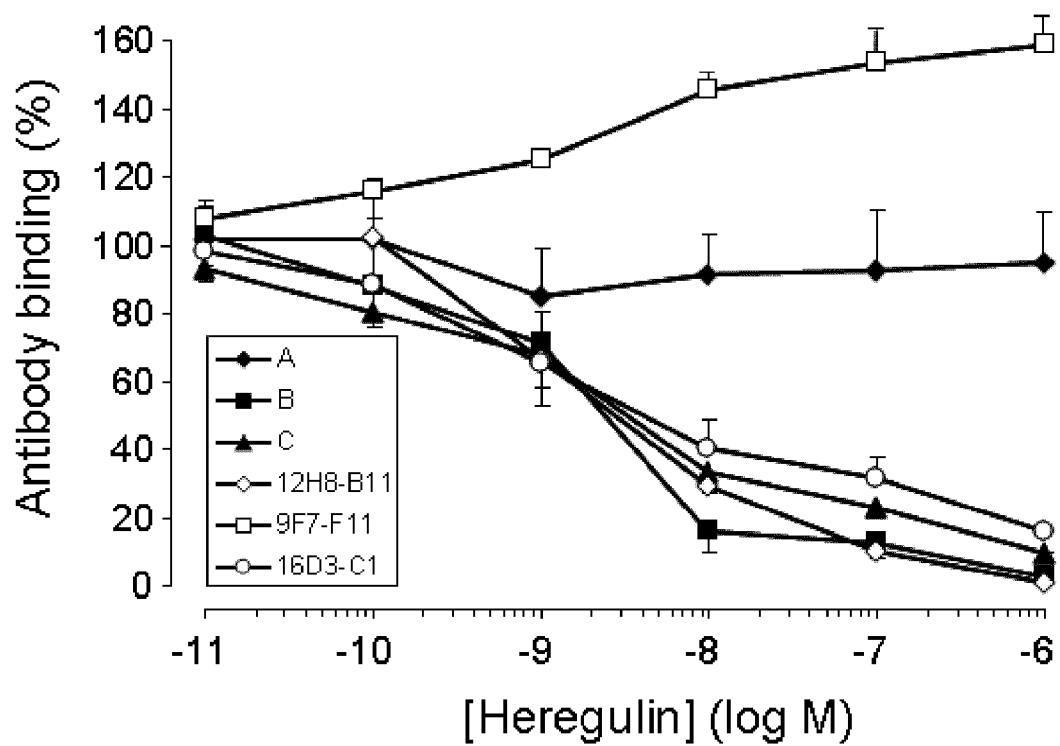

FIG. 5 shows the FACS competition experiment between HER3-specific antibodies 16D3-C1, 9F7-F11 and 12H8-B11 and heregulin on SKBR3 cells. HER3-specific positive control antibodies A, B and C are indicated.

Figure 6:
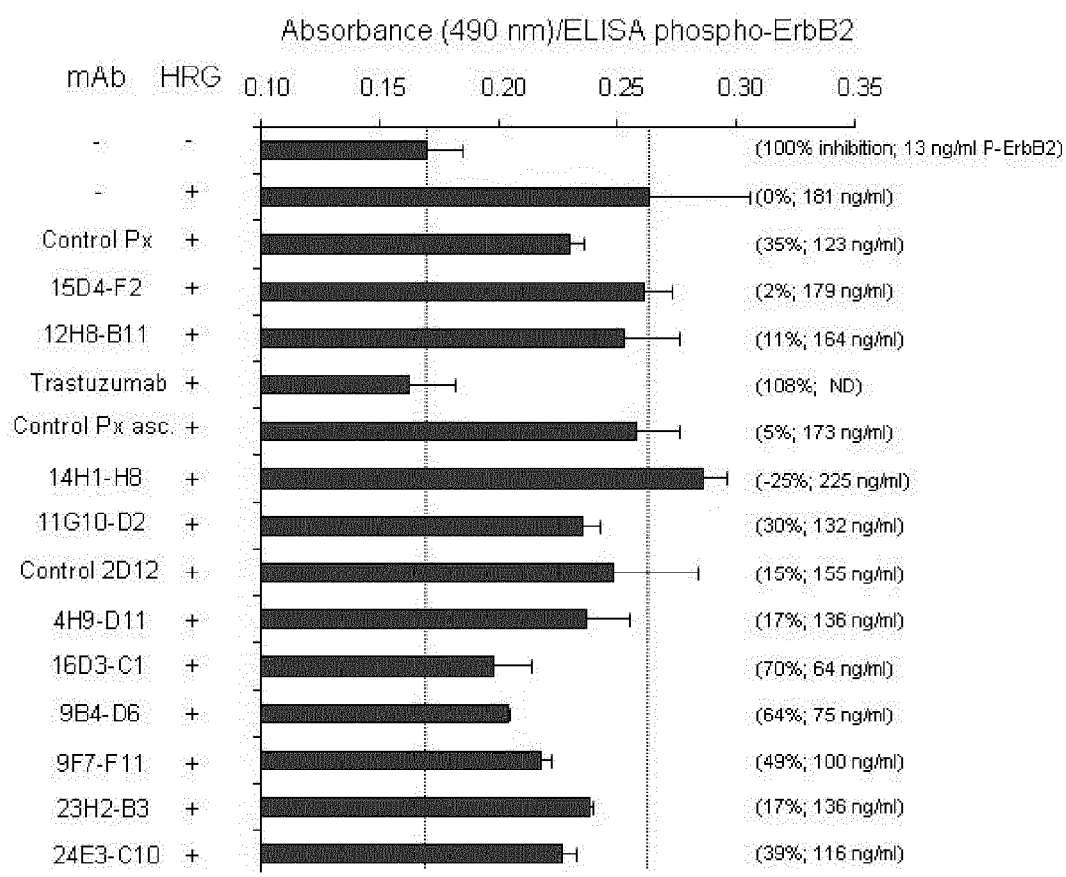

FIG. 6 shows the whole HER2 phosphorylation of HER2/HER3-transfected NIH 3T3 cells treated with anti-HER3 murine mAbs as determined by ELISA.

Figure 7:
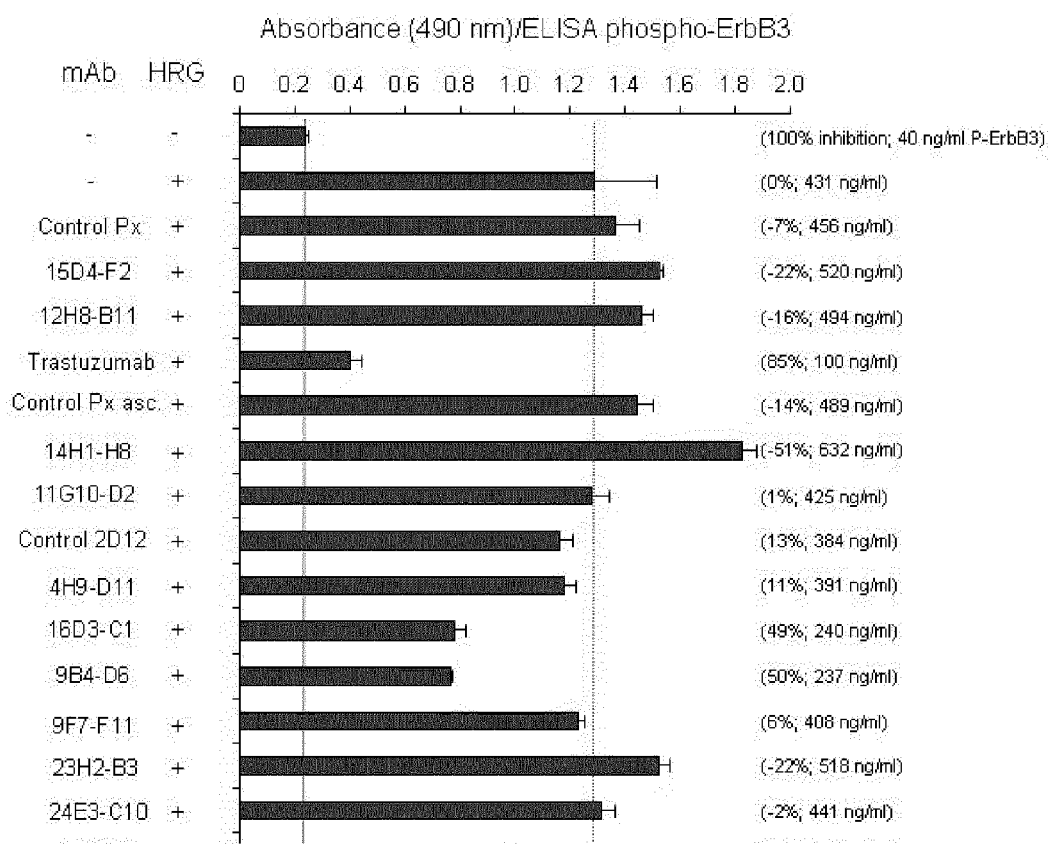

FIG. 7 shows the whole HER3 phosphorylation of HER2/HER3-transfected NIH 3T3 cells treated with anti-HER3 murine mAbs as determined by ELISA.

Figure 8A:
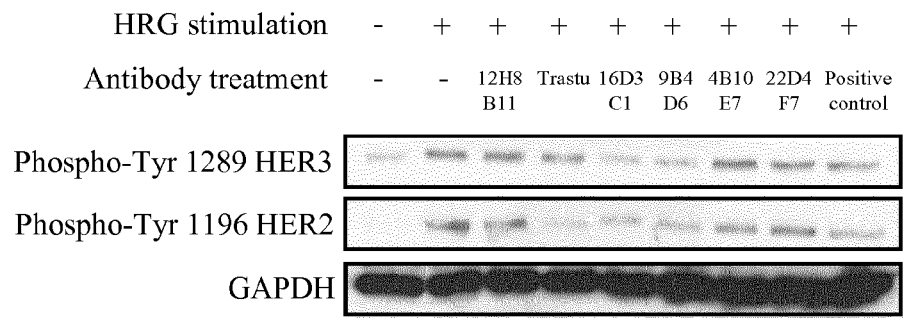
Figure 8B:
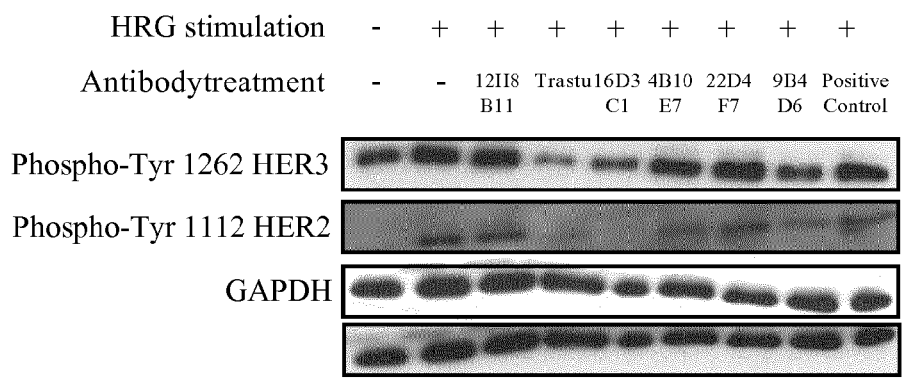

FIG. 8 shows the inhibition of phosphorylation of Y1289 HER3/Y1196 HER2 (A) and Y1262 HER3/Y1112 HER2 (B) by anti-HER3 mAbs in HER2/HER3-transfected NIH 3T3 cells. GAPDH was used as control in the western blots.

Figure 9:
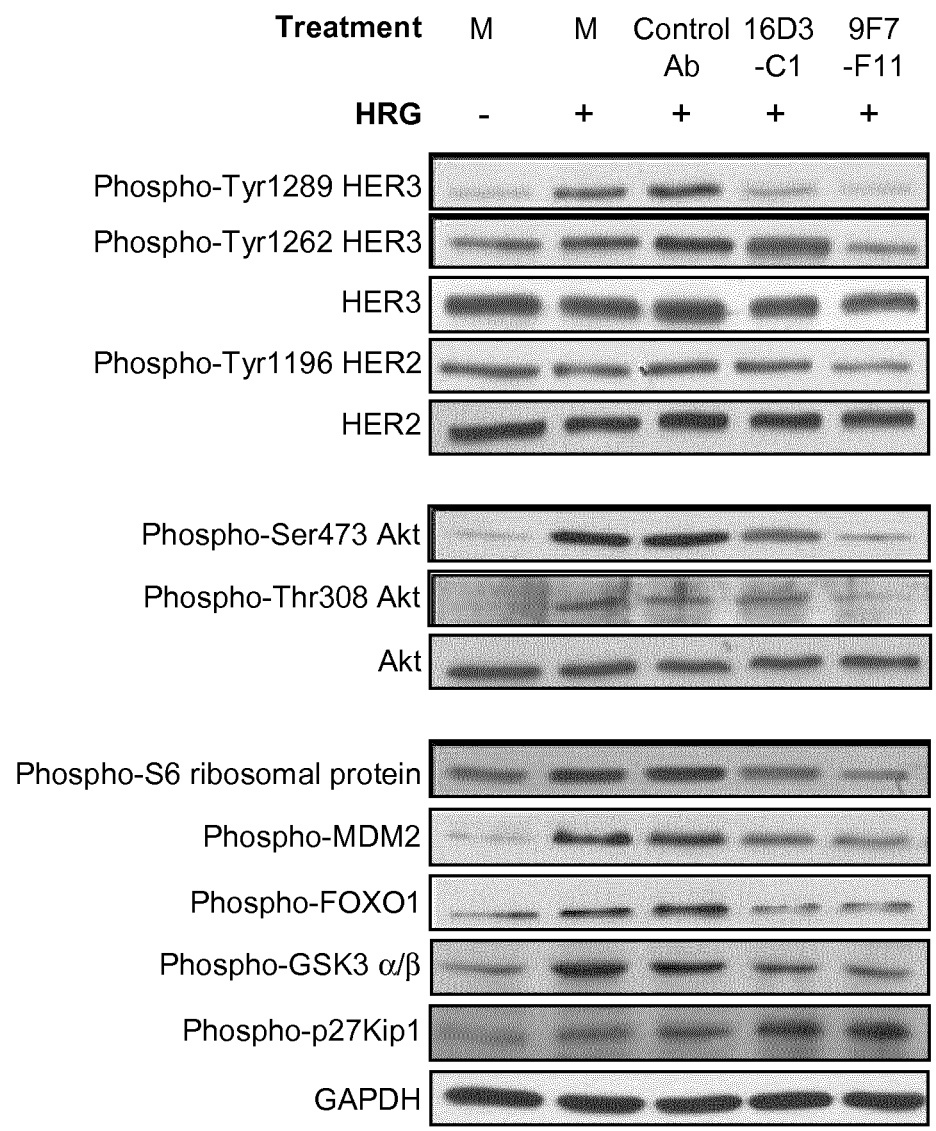

FIG. 9 shows the inhibition of phosphorylation of HER2/HER3 receptors and downstream PI3K/Akt signalling by using anti-HER3 murine mAbs 16D3-C1 and 9F7-F11 in BxPC3 pancreatic carcinoma cells.

FIG. 10 shows antibody-induced inhibition of HER3 internalization in BxPC3 pancreatic carcinoma by western blot (A) and quantification of HER3 internalization (Image J software) (B).

FIG. 11 shows the inhibition of proliferation of HER2/HER3-transfected NIH 3T3 cells and various tumor cell lines by murine HER3-specific antibodies, as measured by the MTS assay.

Figure 12:
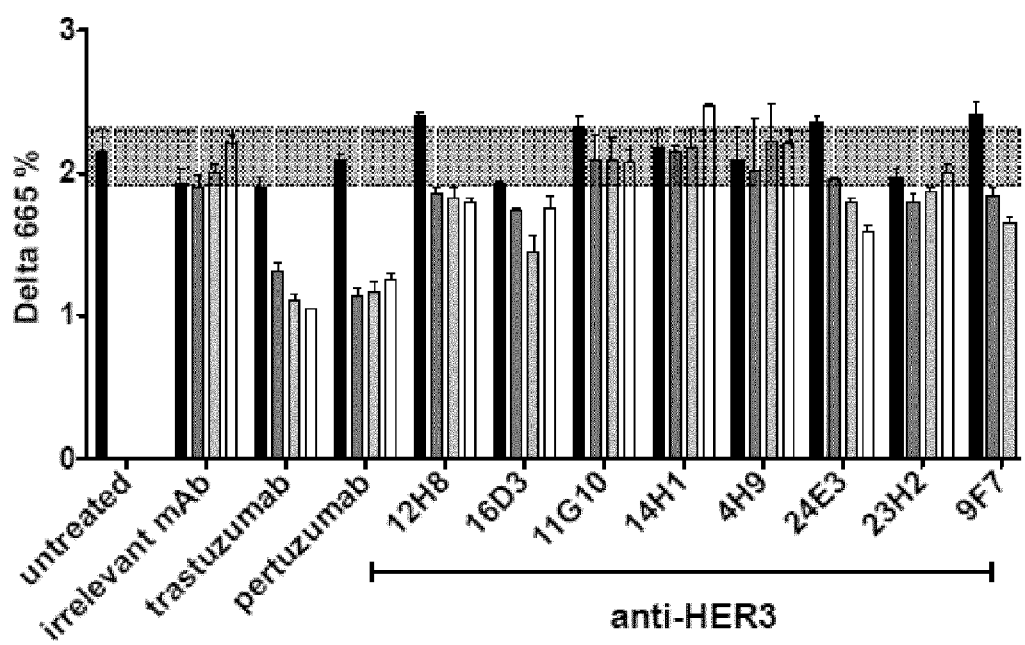

FIG. 12 shows the inhibition of HER2/HER3 heterodimerization by anti-HER3 mAbs in HER2/HER3-transfected NIH 3T3 cells, as measured by TR-FRET analysis.

Figure 13:
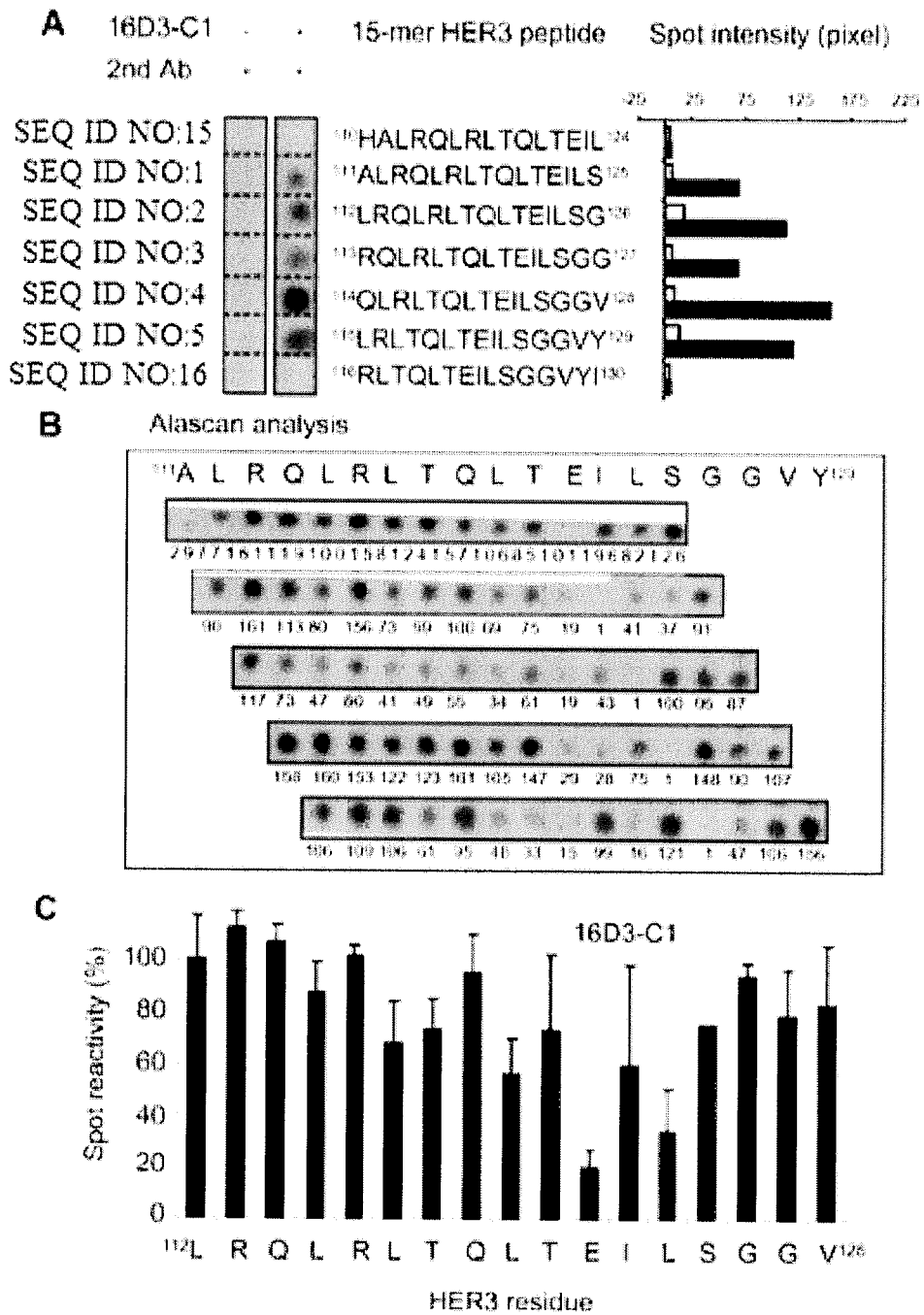

FIG. 13 identifies the epitope recognized by 16D3-C1 mAb. (A) Spot analysis of the region recognized by anti-HER3 antibody 16D3-C1 (SEQ ID NOs: 1-5, 15, and 161 (B) Alascan analysis of the region recognized by 16D3-C1 mAb, and (C) Pixel quantification of 16D3-C1 binding to HER3 peptides (Image J software).

Figure 14:
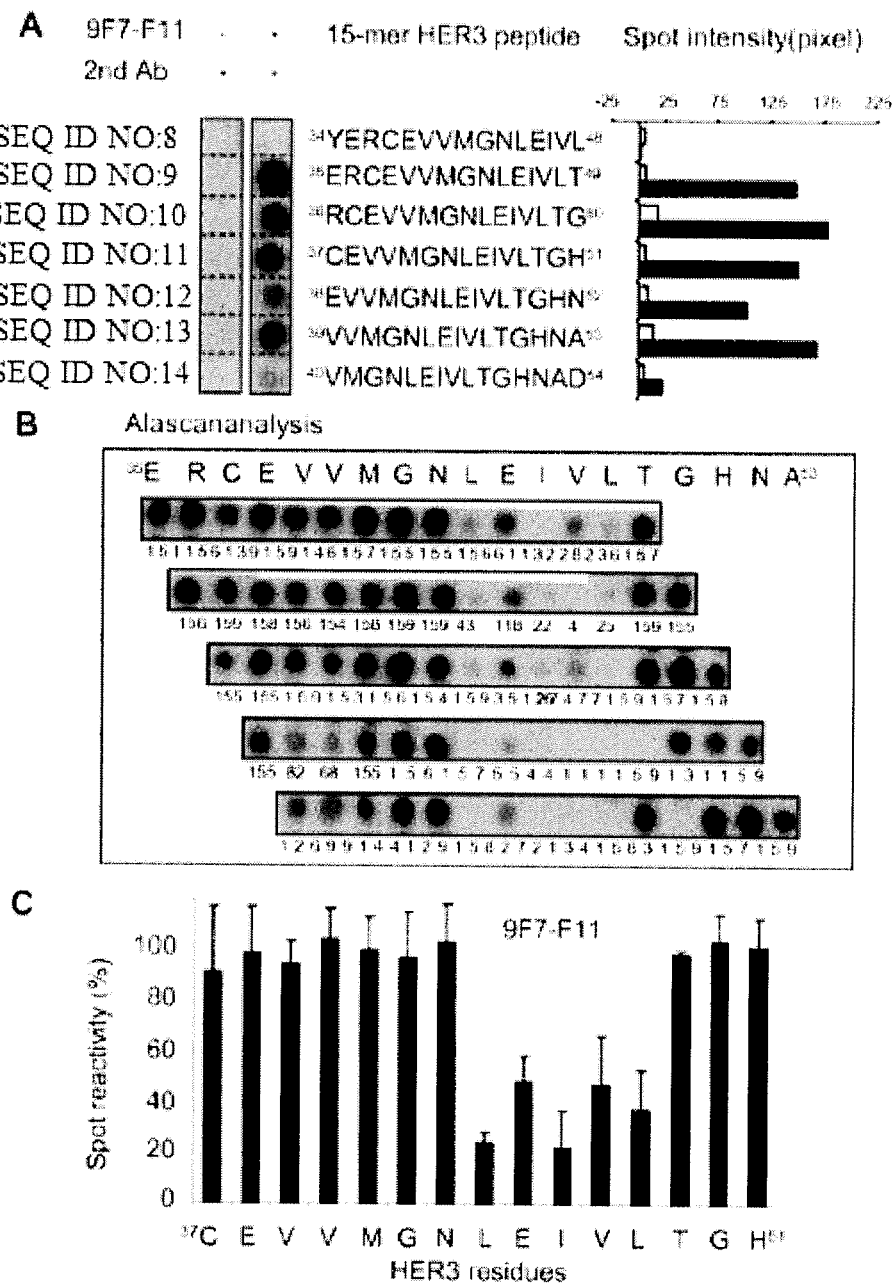

FIG. 14 identifies the epitope recognized by 9F7-F11 mAb. (A) Spot analysis of the region recognized by anti-HER3 antibody 9F7-F11 (SEQ ID NOs: 8-14). (B) Alascan analysis of the region recognized by 9F7-F11 mAb, and (C) Pixel quantification of 9F7-F11 binding to HER3 peptides (Image J software).

Figure 15:
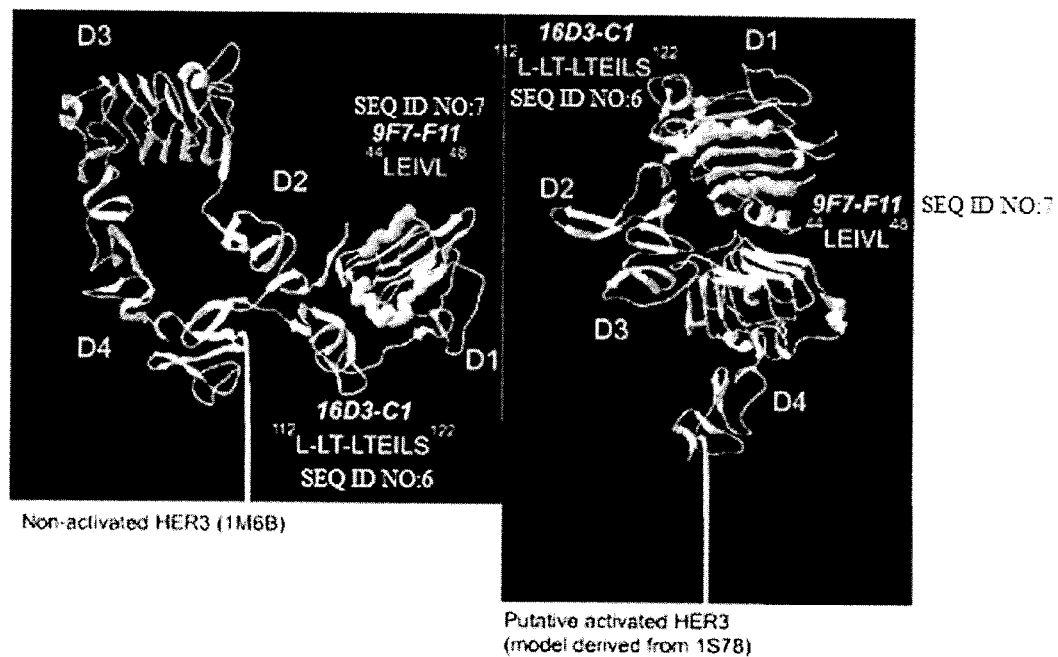

FIG. 15 shows the positioning of Spot-Contributing Residues recognized by mAbs 16D3-C1 (SEQ ID NO: 6) and 9F7-F11 (SEQ ID NO: 7) on the crystallographic structure of unliganded HER3 receptor (pdb 1M6B) (left side), and the superposition on this epitope on the crystallographic structure of the HER2 receptor bound to pertuzumab (pdb 1S78) (right side).

Figure 16:
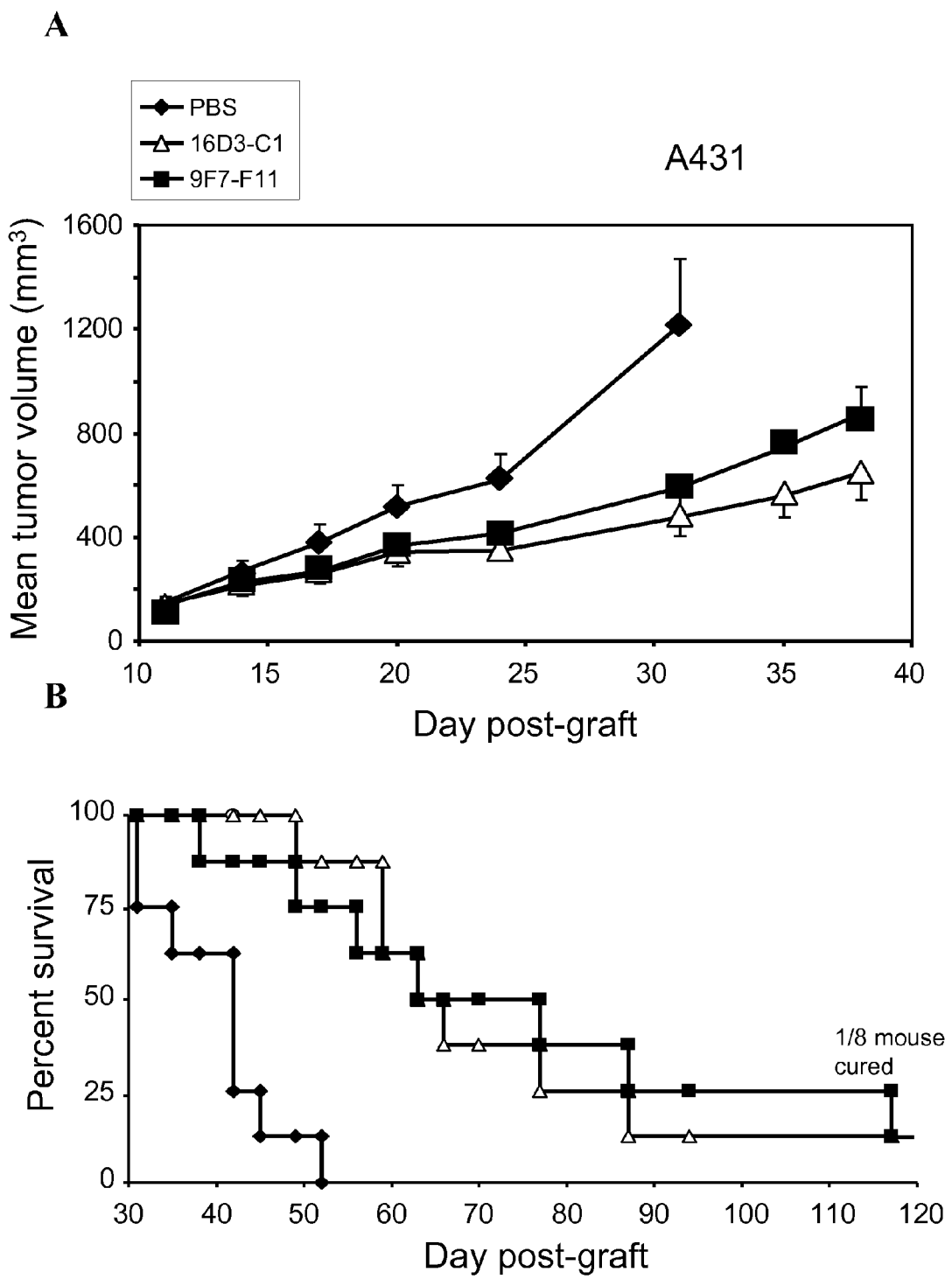

FIG. 16 shows the inhibition of tumor progression by mAbs 16D3-C1 and 9F7-F11 in nude mice xenografted with HRG-addicted, HER2-non amplified/PIK3CA-wt/p53-mut epidermoid A431 cancer cells (A), and the corresponding Kaplan-Meier survival curve (B).

FIG. 17 shows the inhibition of tumor progression by mAbs 9F7-F11 and 16D3-C1 in nude mice xenografted with HER2-non amplified/PIK3CA-wt/p53-wt pancreatic BxPC3 cancer cells (A) and the corresponding Kaplan-Meier survival curve (B).

Figure 18:
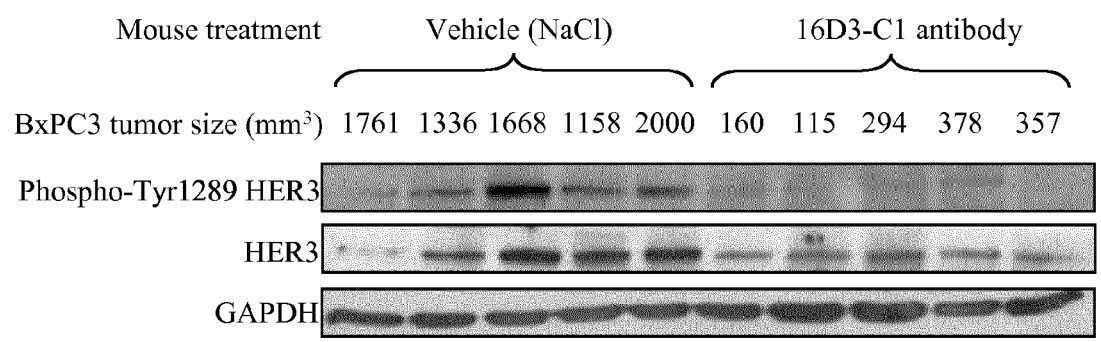

FIG. 18 shows the phosphorylation level of Y1289-HER3 and the whole HER3 expression in extracted BxPC3 xenografts from vehicle- or 16D3-C1-treated mice.

FIG. 19 shows the inhibition of tumor progression by HER3-specific mAb 16D3-C1, used alone or in combination with trastuzumab, in HRG-addicted, HER2$^{low}$ epidermoid A431 (A) and lung A549 (B) cancer cells.

EXAMPLE 1

Mouse Monoclonal Antibody Generation by Immunization

Balb/c Immunization and Generation of Hybridomas.

Monoclonal antibodies against HER3 were developed by sequential immunization of Balb/c mice. The HER3-Fc protein (R&D system) was used as an antigen. A first group of 5 Balb/c mice was subcutaneously injected with 10 µg of soluble HER3-Fc at day 0, day 14 and day 28 in the presence of adjuvant, Freund's complete or incomplete. A second group of 5 Balb/c mice was injected intraperitoneally with HER2/HER3-transfected NIH 3T3 cell line (around $2 \times 10^6$ cells), previously stimulated with heregulin (HRG) to promote HER2/HER3 heterodimer formation. To monitor the antibody response, the antibody titers were measured by ELISA or flow cytometry. Spleen cells from immunized mice were fused according to the protocol already described (Salhi et al. Biochem. J. 2004) using the myeloma PX63Ag8.653. $10^5$ fused cells per well were cultured in plates with HAT media for hybridoma selection. After 12 days post fusion, the hybridoma supernatant screening was performed by ELISA using the protein HER3-Fc as antigen. In control, screenings will be done simultaneously with discriminating antigens HER2-Fc and the Fc fragment alone.

Figure 1A:
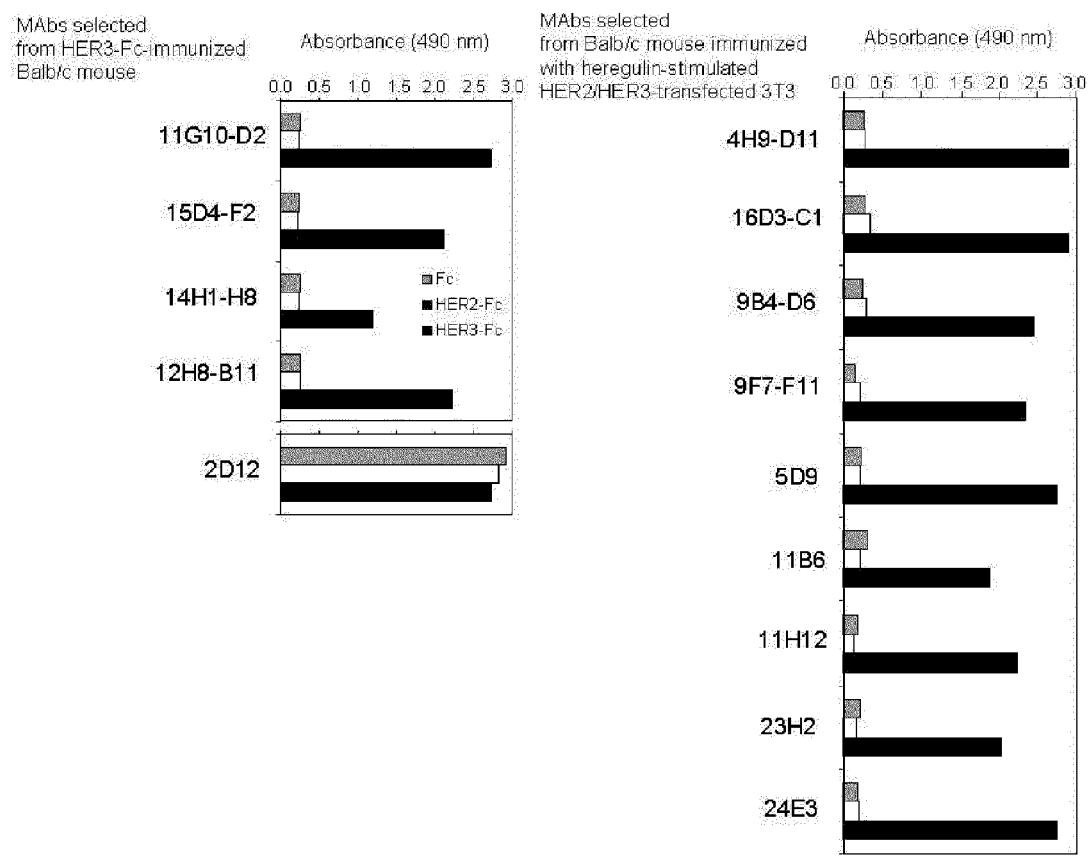
FIG. 1A shows the HER3 vs HER2 and Fc binding of the monoclonal antibodies selected.

As shown in FIG. 1A, thirteen HER3-specific monoclonal antibodies (mAbs) were selected. They are specific to soluble HER3-Fc and do not recognize the Fc moiety. Four anti-HER3 were selected from HER3-Fc-immunized Balb/c mouse and 9 anti-HER3 were selected from Balb/c mouse immunized with heregulin-stimulated HER2/HER3-transfected 3T3 cells. No binding was observed with the HER2-Fc antigen.

The selected anti-HER3 antibodies were compared with two others anti-HER3 antibodies Ab6 (Merrimack Pharmaceuticals) and U1-59 (Amgen/U3 Pharma-Daiichi Sankyo). U1-59 and Ab6 were constructed based disclosure of sequences in patent US2008/0124345A1 and US2009/0291085A1 respectively.

Figure 1B:
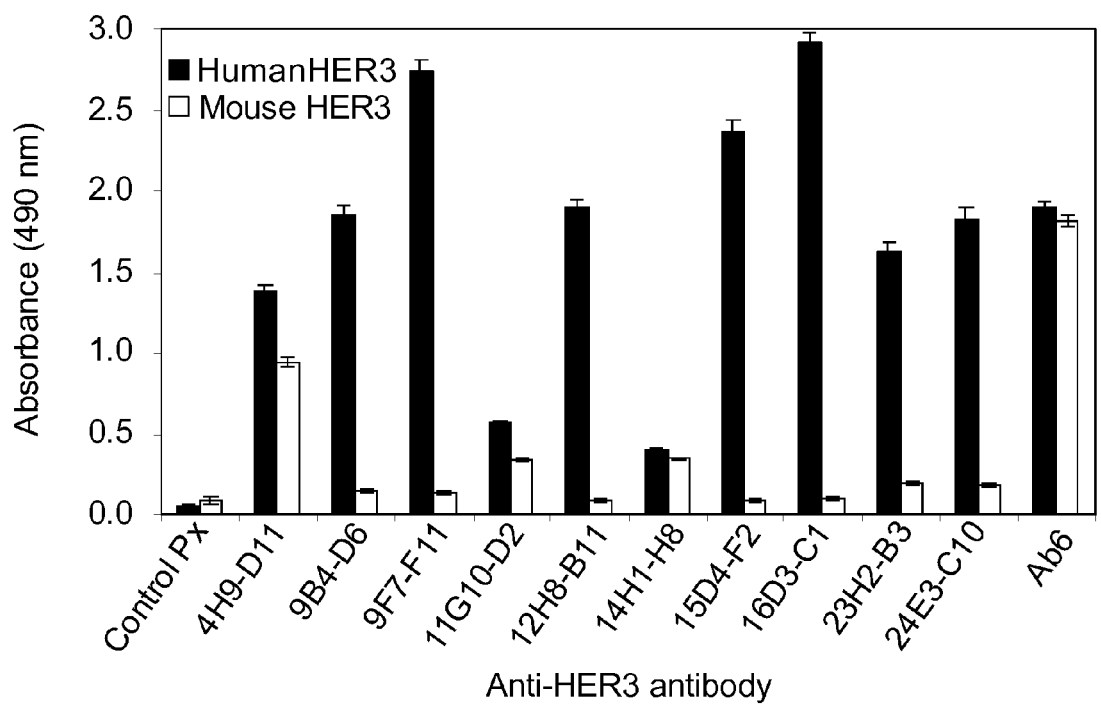
FIG. 1B shows the reactivity of the purified mouse IgG antibodies of the invention towards mouse HER3, with regard to Ab6 antibody.

The cross-reactivity with mouse HER3 receptor was assessed by a comparative ELISA assay with immobilized human HER3-Fc and mouse HER3-Fc (recombinant mouse extracellular domain ErbB3/HER3Fc chimera, R&D Systems) coated at 250 ng/ml. Most of the clones of the invention, at a concentration of 1 µg/ml, did not cross react with mouse HER3 (FIG. 1B) whereas the Ab6 antibody both recognized mouse and human HER3. The clones 9F7-F11 and 16D3-C1 were the best binders. Irrelevant control antibody Px bound neither to human nor to mouse HER3 receptors.

ELISA Binding to HER3

Figure 2A:
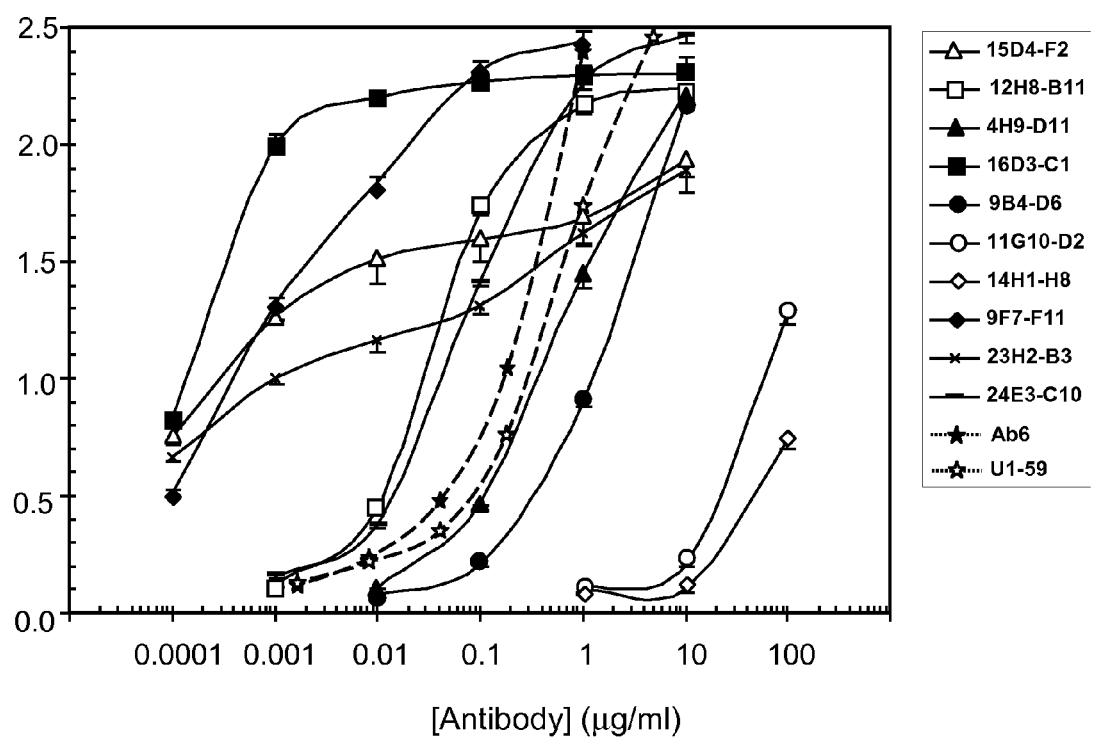
FIG. 2 shows ELISA binding curves (A) and production (B) of purified mAbs to HER3 antigen.

Ninety six-well enzyme immunoassay plates (Nunc, Paisley, UK) were coated overnight at 4° C. with HER3-Fc antigen at a concentration of 250 ng/ml in 160 mM PBS pH 7.2. After four washes in 160 mM PBS pH 7.2, containing 0.1% Tween 20 (PBS-T), plates were saturated with a 1% solution of bovine serum albumin (BSA) in PBS-T buffer for 60 min at 37° C. Two-fold serial dilutions of purified HER3-specific mAbs were added after four washes in PBS-T and plates were incubated at 37° C. for 2 h. Following four washes in PBS-T, 100 µl of a peroxidase-conjugated anti-mouse IgG antibody (Sigma) were added to each well. The conjugate was used at a 1:2000 dilution in PBS-T-1% BSA. The plates were incubated at 37° C. for 60 min and then washed four times in PBS-T. Finally an ortho-phenylenediamine solution (Sigma) was added for 30 min at ambient temperature in the dark and the absorbance was measured at 450 nm. The anti-HER3 mAbs reacted specifically with the HER3 antigen in a dose-specific manner; antibodies 16D3-C1, 9F7-F11, 15D4-F2 and 23H2-B3 being the most reactive (FIG. 2A). In contrast Ab6 and U1-59 antibodies were less reactive for binding to the HER3 receptor. The antibody concentration giving 50% absorbance was less than 1-10 ng/ml for antibodies 16D3-C1, 9F7-F11, 15D4-F2 and 23H2-B3 whereas Ab6 and U1-59 showed a 50%-signal around 200 ng/ml. All the HER3-specific antibodies were produced in ascitic fluid and purified by protein A-immunoaffinity (FIG. 2B).

Flow Cytometry Analysis to HER3-Positive Cells

EGFR-, HER2-, HER3-, HER2/HER3- and EGFR/HER4-transfected NIH 3T3 fibroblasts ($10^6$ cells) were incubated with the anti-HER3 mAbs in PBS-BSA 0.1% at 4° C. for 1 h. After three washes in PBS-BSA 0.1%, cells were incubated with the fluorescein-conjugated anti-mouse IgG (1:50) (Sigma) at 4° C. in the dark for 45 min. Cells were then washed three times and suspended in PBS for analysis using an EPICS flow cytometer (Beckman-Coulter, Fullerton, Calif.). As shown in FIG. 3, all the HER3-specific mAbs bound to HER3- and HER2/HER3-, but not to wild-type-, EGFR-, HER2- and EGFR/HER4-transfected NIH 3T3 cells. Binding for HER2/HER3-transfected NIH3T3 cells (geometric mean) was higher for antibodies 9B4-D6, 12H8-B11, 15D4-F2 and 16D3-C1 than for antibodies Ab6 and U1-59.

Affinity Measurement by BIACORE

HER3 binding of selected antibodies was confirmed by BIACORE analysis (FIG. 4). BIACORE analysis has been performed using the interaction analysis facilities located at the Cancer Research Institute in Montpellier (PP2I platform, M. Pugnière). The kinetic parameters of the binding of the HER3 receptor to selected antibodies were determined at 25° C. by surface plasmon resonance analysis using a BIACORE 3000 instrument (GE Healthcare, Uppsala, Sweden). HER3-specific antibodies were immobilized on the CM5 sensor chip surface using a captured rabbit anti-mouse polyclonal antibody (Sigma-Aldrich). The captured antibody was immobilized according to the manufacturer's instructions. The HER3 receptor in HBS-EP buffer containing 10 mM Hepes (pH 7.4), 3 mM EDTA, 150 mM NaCl, and 0.005% non-ionic surfactant P20 (GE Healthcare) was then injected at a concentrations of 50 µg/ml over the flow cell, and the dissociation phase was followed by a regeneration step with 10 mM HCl solution (FIG. 4). The flow rate was 50 µl/min. All the sensorgrams were corrected by subtracting the control flow cell signal. The data were globally fitted to a bivalent analyte model using BIAevaluation Version 4.1.1 software FIG. 4). The association rate ($k_a$) for the selected antibodies ranged around $1 \times 10^5$ $M^{-1}s^{-1}$, quite similar than those obtained for Ab6 antibody (Tab. 6). In contrast, dissociation constant for each antibody was more variable explaining why we observed notable differences in $K_D$ values. Antibodies 16D3-C1, 12H8-B11 and 9F7-F11 showed the best affinities, in a range of 1-5 nM, similarly as the value measured for Ab6 antibody.

TABLE 6

| Antibody | $k_a$ $M^{-1}s^{-1}$ | $k_d$ $s^{-1}$ | $K_D$ nM |
|---|---|---|---|
| 9F7-F11 | $5.4 \times 10^4$ | $2.4 \times 10^{-4}$ | 4.4 |
| 11G10-D2 | $3.5 \times 10^5$ | $7.9 \times 10^{-3}$ | 22.6 |

TABLE 6-continued

| Antibody | $k_a$ $M^{-1}s^{-1}$ | $k_d$ $s^{-1}$ | $K_D$ nM |
|---|---|---|---|
| 12H8-B11 | $6.6 \times 10^4$ | $1.6 \times 10^{-4}$ | 2.4 |
| 14H1-H8 | $1.3 \times 10^5$ | $4.0 \times 10^{-3}$ | 30.7 |
| 15D4-F2 | $2.3 \times 10^5$ | $1.4 \times 10^{-2}$ | 63.7 |
| 16D3-C1 | $8.7 \times 10^4$ | $8.9 \times 10^{-5}$ | 1.0 |
| Ab6 | $9.3 \times 10^4$ | $3.1 \times 10^{-4}$ | 3.3 |

Competition with Heregulin

Cytometry competition experiments were performed in order to quantify the ability of HRG to inhibit antibody binding to HER3 in a SKBR3 cell-based assay. To this end, $10^5$ SKBR3 cells were pre-incubated with various concentrations of the competing HRG ligand for 1.5 h on ice. After one washing with PBS-1% BSA, anti-HER3 mAbs, at concentration giving 50% maximal binding, were added to each well for 1 h on ice. In some experiments, HRG ligand and anti-HER3 antibodies were co-incubated for 2 h on ice. Cells were then washed and further incubated with a 1:60 dilution of appropriate FITC-conjugated secondary antibody (Sigma) for 45 min on ice, before cytometry analysis on a Quanta apparatus (Beckman-Coulter). Competition experiments by FACS demonstrated that 9F7-F11 antibody did not compete with heregulin, thus suggesting that this antibody did not bind to the HRG-binding site (FIG. 5). 9F7-F11 antibody binding was even enhanced when HRG was added, whereas binding of the positive control antibody A was not modified by HRG incubation. In contrast, antibodies 12H8-B11 and 16D3-C1, as well as positive-control antibodies B and C, showed a HRG-dependent binding decrease to the HER3 receptor, demonstrating that epitopes recognized by these antibodies are closed or located to the HRG-binding site, or could be sterically-impaired for antibody binding when HRG induces transconformation of active HER3 receptor for dimerization (FIG. 5). Inhibitory concentration leading to 50% binding ranged around 2.5 nM of HRG ligand for antibodies 12H8-B11 and 16D3-C1. Similar results were obtained either by sequential or co-incubation of HRG with antibodies.

EXAMPLE 2

Inhibition of HER2 and HER3 Phosphorylation by Anti-HER3 Antibodies of the Invention HRG Stimulation of Transfected NIH 3T3 Fibroblasts A total of $8 \times 10^4$ ErB2/HER3-transfected NIH 3T3 cells were cultured in 6-well plates for 72 h in RPMI-FCS 5% and for a further 24 h in RPMI-FCS 1%. Cells were then incubated with HER3-specific mouse mAbs at a concentration of 20 µg/ml in RPMI-FCS 1% for 1 h at 37° C. After removing the antibodies, ligand stimulation was performed by incubating the antibody-treated cells with a solution of 100 ng/ml HRG for 10 min at 37° C. After washing in cold Dulbecco-PBS (D-PBS), cells were twice scraped from plastic dishes using a rubber policemen in 0.5 ml cold D-PBS. After a 1 min-centrifugation at 11,000 g, cell pellets were lysed in 50 µl of lysis buffer containing 20 mM Tris pH 7.5, 150 mM NaCl, 1.5 mM $MgCl_2$, 1 mM EDTA, 1% Triton X-100 (v/v), 10% glycerol (v/v), 100 mM sodium fluoride, 0.1 mM phenylmethylsulfonyl fluoride, 1 mM sodium orthovanadate (Sigma), and one complete protease inhibitor mixture tablet (Roche Diagnostics, Meylan, France). After incubation of 30 minutes, samples were cleared of insoluble fraction by centrifugation and protein concentrations in cell lysates were determined by Bradford colorimetric reaction.

ELISA Measurement of HER2 and HER3 Whole Phosphorylation in HER2/HER3-transfected 3T3 fibroblasts Tyrosine-phosphorylated HER2 and HER3 in cell lysates were quantified using DuoSet® sandwich ELISA (RD Systems, Minneapolis, Minn.), as described by the manufacturer. As shown in FIG. 6 and FIG. 7, mAbs 16D3-C1 and 9B4-D6 inhibited HER2 and HER3 whole phosphorylation, as does control trastuzumab. Mabs 9F7-F11 and 24E3-C10 blocked phosphorylation of HER2.

PAGE-SDS and Western Blot Analysis of Y1112 and Y1196 HER2 Phosphorylation Vs Y1262 and Y1289 HER3 Phosphorylation in HER2/HER3-Transfected 3T3 Fibroblasts After Electrophoresis on 7% SDS-PAGE Under Reducing Conditions, the Cell Lysates were transferred to polyvinylidene difluoride membranes (Millipore, Molsheim, France) which were saturated in 25 mM Tris pH 7.4, 150 mM NaCl buffer containing 0.1% Tween 20 (TNT) and 5% nonfat dry milk for 1 h at ambient temperature. A 1 µg/ml solution in TNT-BSA 5% of antibodies directed to HER2-phosphorylated Y1112 (Millipore) or Y1196 (RD Systems), and directed to HER3-phosphorylated Y1262 (RD Systems) or Y1289 (Cell Signaling Technology) were incubated for 18 h at 4° C. After five washes in TNT, blots were incubated with peroxidase-conjugated mouse-specific ($1/2000$) or rabbit-specific ($1/10000$) antibodies (Sigma) as appropriate, for 1 h in TNT-5% nonfat dry milk at ambient temperature. After 5 washes in TNT, the blots were visualized using chemiluminescent substrate (Western Lightning Plus-ECL, Perkin Elmer). As indicated by western blot in FIGS. 8A and 8B, mAbs 16D3-C1 and 9B4-D6 blocked Y1196 and Y1112 HER2 phosphorylation, and Y1262 and Y1289 HER3 phosphorylation, as did control trastuzumab.

Inhibition of Phosphorylation and Internalization of the HER3 Receptor in BxPC3 Pancreatic Carcinoma Cells Five hundred and thousand BxPC3 tumor cells were added to each well of a 6-well culture plate for 24 h at 37° C. After serum starvation for 16 h in a RPMI complete medium with 1% FCS and further washing, cells were pre-incubated with a 50 µg/ml concentration of antibodies 16D3-C1 and 9F7-F11, or negative control antibody for 15 min at 37° C., before washing and subsequent stimulating or not with a 100 ng/ml dilution of heregulin. Cells were then washed, scraped and lysed with buffer containing 20 mM Tris-HCl pH 7.5, 150 mM NaCl, 1.5 mM $MgCl_2$, 1 mM EDTA, 1% Triton, 10% glycerol, 0.1 mM Phenylmethylsulfonyl fluoride, 100 mM sodium fluoride, 1 mM sodium orthovanadate (Sigma-Aldrich), and one complete protease inhibitor mixture tablet (Roche Diagnostics, Indianapolis, Ind.). After a 30 min-incubation time, samples were cleared of insoluble fraction by centrifugation and protein concentrations in cell lysates were determined by Bradford assay. These protein lysates were directly mixed with Laemmli buffer (1-20 µg total proteins depending on the target and cell lines) and heated at 95° C. for 5 minutes. After electrophoresis on 7% SDS-PAGE under reducing conditions, the proteins were transferred to polyvinylidene difluoride membranes (Millipore) which were then saturated in TNT buffer (Tris 25 mM pH 7.4, NaCl 150 mM, Tween 0.1%) containing 5% nonfat dry milk for 1 h at 25° C. Primary antibodies, directed to kinase receptors or signaling kinases, and their phosphorylated forms, were incubated in TNT-5% BSA buffer for 18 h at 4° C. After five washes in TNT buffer, peroxidase-conjugated rabbit, goat or mouse polyclonal antibodies (Sigma-Aldrich) were added as appropriate in TNT buffer containing 5% nonfat dry milk for 1 h at 25° C. After five washes in TNT buffer, the blots were visualized using a chemiluminescent substrate (Western lightning Plus-ECL, Perkin Elmer).

Remarkably, antibodies 16D3-C1 and 9F7-F11 blocked ligand-induced phosphorylation on HER3 residues Y1289 and Y1262 (FIG. 9); antibody 9F7-F11 being the most efficient one. Inhibition of Akt phosphorylation on Ser473 and Thr308 was concomitantly demonstrated following a 15 min short-time treatment of antibodies 16D3-C1 abd 9F7-F11 on BxPC3 cells. Phosphorylation of AKT-triggered downstream signalling was also affected by the selected antibodies, i.e. inhibition of the phosphorylation of phospho-S6 ribosomal protein which reduces protein synthesis, blockade of phosphorylation of FoxO1a which favors gene nuclear transcription leading to apoptosis and cell cycle arrest, decrease of phospho-MDM2 which prevents p53 degradation, and inhibition of phospho-GSK3α/β which blocks the cell cycle and favors apoptosis (FIG. 9).

Figure 10A:
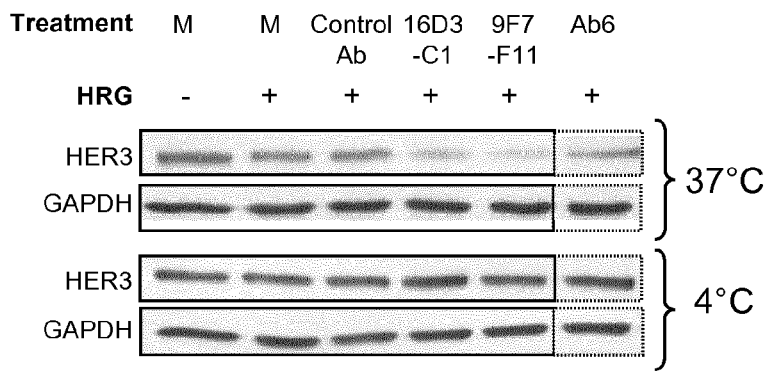
Figure 10B:
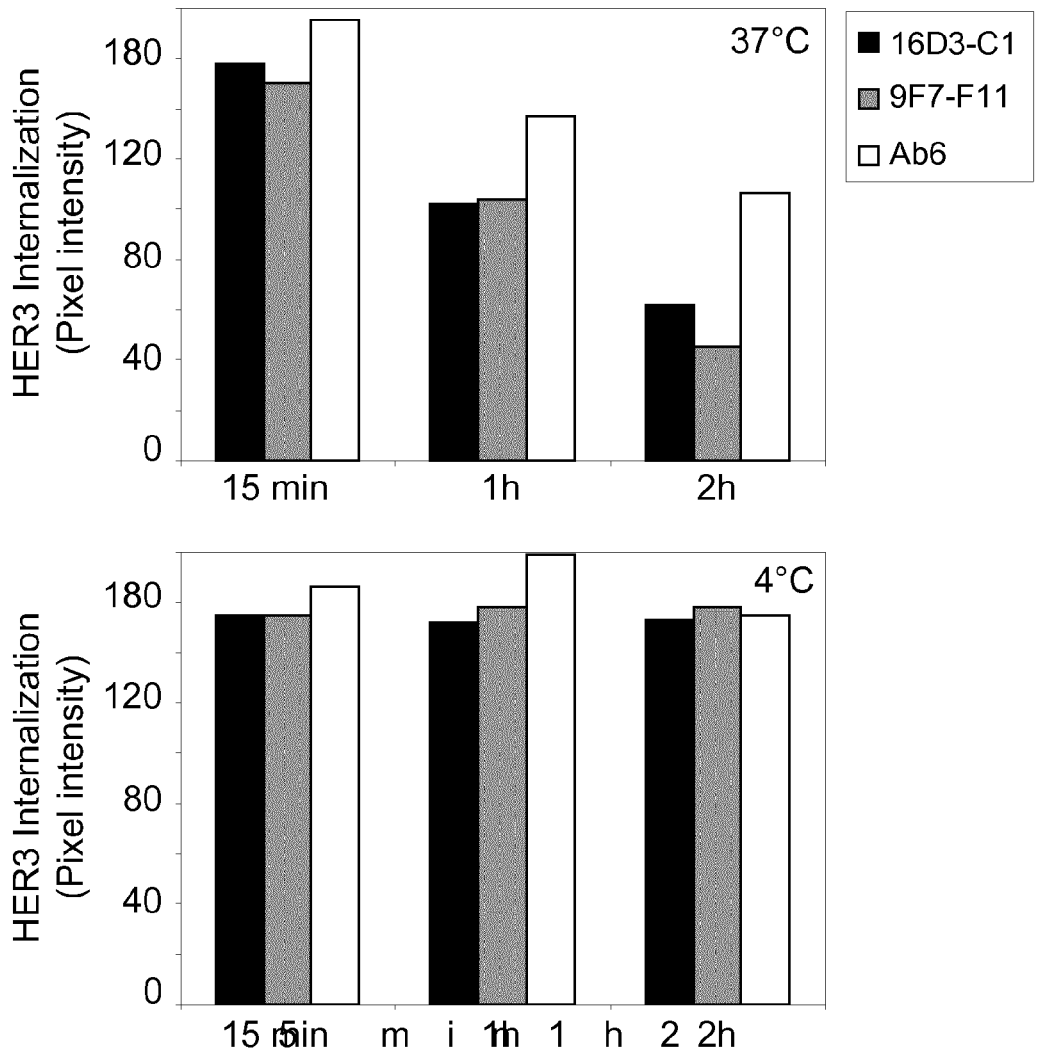

BxPC3 cells were analyzed for cell surface expression of the HER3 receptor after exposure to 9F7-F11 and 16D3-C1 antibodies for different times and temperatures. As shown on FIG. 10A, a 2 h-antibody incubation of BxPC3 cells at 37° C. strongly reduced HER3 cell surface expression. Such antibody-induced HER3 down-regulation was abrogated when cells were treated at 4° C., thus demonstrating that HER3-specific antibodies 9F7-F11 and 16D3-C1 induced HER3 internalization. In contrast HER3 internalization was lower when BxPC3 cells were treated with Ab6 antibody (FIG. 10A). Quantification of HER3 internalization confirmed that 16D3-C1 and 9F7-F11 antibodies are more efficient than Ab6 to induce HER3 internalization (FIG. 10B). A 2 h-antibody treatment induced 73% and 78% HER3 internalization with antibodies 16D3-C1 and 9F7-F11 respectively, and only 42% internalization for Ab6 antibody (FIG. 10B).

EXAMPLE 3

Inhibition of Cell Proliferation

A total of $10^4$ HER2/HER3-transfected NIH 3T3 fibroblasts were cultured in 96-well plates for 24 h in DMEM complete medium. Cells were then incubated with anti-HER3 antibodies at a final concentration of 100 µg/ml for 5 days at 37° C. Proliferation was measured by adding 40 µl/well of a solution containing the tetrazolium compound MTS [3-(4,5-dimethylthiazol-2-yl)-5-(3-carboxymethoxyphenyl)-2-(4-sulfophenyl)-2H-tetrazolium] and the electron coupling reagent PMS (phenazine methosulfate). MTS is reduced by cells into a formazan product that is soluble in tissue culture medium. The absorbance of the formazan at 490 nm can be measured using a spectrophotometer. As shown in FIG. 11, mAbs 16D3-C1 and 9F7-F11 inhibited 23.7% and 32.0% of the proliferation of HER2/HER3-transfected NIH 3T3 fibroblasts, respectively. No significant inhibition of HER2/HER3-transfected NIH 3T3 was observed with the other HER3-specific antibodies. In addition, 16D3-C1 and 9F7-F11 inhibited the proliferation of A431 epidermoid carcinoma, breast cancer cell line MCF7 and MDA-MB361, epithelial ovarian tumors from primary ascites 1 (clone A5) and 2 (clone C9), metastasis 2815, and OVCAR3 and SKOV3 cell lines. The proliferation of breast cancer cell line T47D, and A549 lung carcinoma were inhibited by mAb 9F7-F11 solely.

EXAMPLE 4

Measurement of Antibody-Induced Inhibition of HER2/HER3 Heterodimerization by Time Resolved-Fluorescence Resonance Energy Transfer (TR-FRET)

The assay was performed on adherent cells using an anti-HER2 (FRP5) and an anti-HER3 (15D4-F2) respectively labeled with Lumi4-terbium cryptate and D2 acceptor dye (Cisbio Bioassays). These mAbs were chosen due to their targeting epitopes different from studied mAbs of interest. HER2/HER3-transfected NIH 3T3 cells were plated for 24 h at $3\times10^5$ per well in 96-wells sterile black microplate in DMEM medium (without phenol red) supplemented with 10% of fetal calf serum. They were treated with various concentrations of HER3-specific murine mAbs for 30 min at 37° C. After washing in KREBS buffer, cells were then fixed 2 min in 10% formalin (Sigma-Aldrich) and washed once with KREBS. After incubation with labeled antibodies (5 nM each) diluted in KREBS for 6 hours at 37° C., the cells were washed 4 times with KREBS buffer. The fluorescence of Lumi4-terbium and D2 were measured respectively at 620 and 665 nm (60 μs delay, 400 μs integration) upon 337 nm excitation on a Pherastar FS instrument. Serial dilutions of the Lumi4-terbium labeled antibodies in KREBS were simultaneously measured on the same microtiter plate, and the 665 nm emission was plotted against the 620 nm emission. The resulting curve was used to compute the 665 nm contribution from the terbium ($E665_{Tb}$) using the 620 nm emission (E620) of the samples. The TR-FRET signal was expressed as $\Delta 665$ (%)=$\Delta 665/665_{Tb}$, with $\Delta 665 = E665c - E665_{Tb}$; the 665 nm and 620 nm emissions from the samples were corrected from background as $E665c = E665_{sample} - E665_{background}$ and $E620c = E620_{sample} - E620_{background}$. The $E665_{background}$ and $E620_{background}$ being measured on a blank containing only the reading buffer. The TR-FRET signal expressed as $\Delta 665(\%)$ represent the HER2/HER3 dimer quantity. The 620 nm time resolved fluorescence emission is correlated with HER2 quantity. At the same time, the prompt fluorescence of D2 was measured at 670 nm upon 620 nm excitation to quantify HER3 receptors. For each sample, controls were obtained by performing the same experiment with untreated cells or with cells treated with irrelevant antibody, trastuzumab and pertuzumab. As shown in FIG. 12, mAbs 16D3-C1, 24E3-C10 and 9F7-F11 induced a dose-dependent inhibition of HER2/HER3 heterodimerization whereas the others antibodies (and particularly 12H8-B11) did not. No blockade was observed with irrelevant antibody. Pertuzumab, as well as trastuzumab, strongly induced dimer inhibition.

EXAMPLE 5

Epitope Mapping of Anti-HER3 Antibodies

Membranes were obtained from Abimed (Langenfeld, Germany). Fmoc amino acids and N-hydroxybenzotriazole were obtained from Novabiochem (Laufelfingen, Switzerland). The ASP222 robot (Abimed) was used for the coupling steps. Two hundred-and-thirteen overlapping dodecapeptides frameshifted by one residue, representing the extracellular domain of HER3 receptor, were synthesized on cellulose membranes. All peptides were acetylated at their N-terminus. After the peptide sequences were assembled, the side-chain protecting groups were removed by trifluoroacetic acid treatment. After three washings in TBS buffer (137 mM NaCl, 2.68 mM KCl, 50 mM Tris), the membrane was saturated with TBS buffer containing 0.1% Tween 20 (TBS-T) and 2% semi-skimmed milk for 18 h at 4° C. After one washing in TBS-T, a 1 μg/ml solution of the anti-HER3 mAbs 16D3-C1 and 9F7-F11 was added to the membrane for 1 h30 at 37° C. Bound antibody was detected by incubation of the membrane at 37° C. for 1 h in a 1:2000 dilution of a peroxidase-conjugated anti-mouse IgG (Sigma, St Louis, Mo.), and subsequent electrochimioluminescent revelation. 16D3-C1 mAb recognized region 111-129 (FIG. 13A) whereas 9F7-F11 mAb bound region 35-53 (FIG. 14A); these two regions being located on the D1 domain of the HER3 receptor.

To precisely identify the epitopes recognized by these antibodies, Spot alanine scanning analysis was performed. Twelve pentadecapeptides corresponding to antibody-immunoreactive amino acid sequences previously identified in FIGS. 13A and 13B, and the fifteen alanine analogs of each peptide were synthesized by the Spot method. Antibody reactivity of cellulose-bound peptides was assayed similarly as described above. The reactivity of the spots was evaluated by scanning the membrane and measuring the intensities of the spots with the Image J software 1.44 (http://rsbweb.nih.gov/ij). Spot Contributing Residues (SCR), belonging to the HER3 epitopes recognized by mAbs 16D3-C1 and 9F7-F11 were identified on the basis of decreased antibody-binding capacity equal or superior to 20% of that of the unmodified peptide sequence. Study of the five pentadecapeptides $^{111}$ALRQLRLTQLTEILS$^{125}$ (SEQ ID NO:1), $^{112}$LRQLRLTQLTEILSG$^{126}$ (SEQ ID NO:2), $^{113}$RQLRLTQLTEILSGG$^{127}$ (SEQ ID NO:3), $^{114}$QLRLTQLTEILSGGV$^{128}$ (SEQ ID NO:4) and $^{115}$LRLTQLTEILSGGVY$^{129}$ (SEQ ID NO:5) from HER3/D1 domain (FIG. 13B) identified $^{112}$L-LT-LTEILS$^{122}$ (SEQ ID NO:6) as the binding motif for mAb 16D3-C1, with Leu$^{120}$, Glu$^{122}$, Ile$^{123}$ and Leu$^{124}$ being the main SCRs (FIG. 13C). The anti-HER3 antibody 9F7-F11 recognized the motif $^{44}$LEIVL$^{48}$ (SEQ ID NO:7) in the HER3/D1 domain (FIG. 14B), in which residues Leu$^{44}$, Ile$^{46}$ and Leu$^{48}$ were identified as SCRs (FIG. 14C).

We performed positioning of SCRs from the binding motifs of antibodies 16D3-C1 and 9F7-F11 on the crystallographic structure of unliganded HER3 receptor (pdb 1M6B) (FIG. 15, left). The 9F7-F11 epitope $^{44}$LEIVL$^{48}$ layered in one of the prominent β-strands at the beginning of domain 1, facing to domain 3 at 60 Å-distance, and overhanging the D2 domain. The 16D3-C1 binding motif was more deeply located inside the β-strand structure of D1 domain. At present, no crystal structure of HER3 receptor bound to a ligand has been reported. By sequence homology, the epitopes recognized by HER3-specific antibodies 16D3-C1 and 9F7-F11 were superimposed on the crystallographic structure of the HER2 receptor bound to pertuzumab (pdb 1S78) (FIG. 15, right).

EXAMPLE 6

Xenograft Tumor Studies

Athymic, 6- to 8-week-old, female BALB/c nude mice were purchased from Janvier and Charles Rivers Laboratories. HER2-non amplified/PIK3CA-wt/p53-mut epidermoid A431 ($1\times10^6$), HER2-non amplified/PIK3CA-wt/p53-wt pancreatic BxPC3 ($3.5\times10^6$) and HER2-non amplified/PIK3CA-wt/p53-wt lung A549 ($5\times10^6$) cancer cells were injected s.c. into the right flank of athymic BALB/c nude mice. They both expressed HER3 receptor at low level (between 10000 and 20000 receptors/cell). In add, A431 and A549 cancer cells secreted HER3 ligand HRG and are HRG-addicted (Yonesaka, 2011, Zhou 2006).

All in vivo experiments were done in compliance with the French guidelines for experimental animal studies (Agreement no. B34-172-27).

Tumor-bearing mice were randomized in the different treatment groups when the tumors reached an approximate volume of 100 mm³. The mice were treated by i.p. injections of HER3-specific antibodies 16D3-C1 or 9F7-F11 vs vehicle (PBS). The amount of injected antibody was 300 μg/injection, three-time week (Q2d, 15 mg/kg), for 6 weeks consecutively. Tumor dimensions were measured twice weekly with a caliper and the volumes were calculated by the formula D1×D2×D3/2. Tumor progression was calculated using the formula [(final volume)−(initial volume)]/(initial volume). The results were also expressed by a Kaplan-Meier survival curve, using the time taken for the tumor to reach a determined final volume of 2,000 mm³. A median delay was defined as the time at which 50% of the mice had a tumor reaching the determined volume.

A431 cancer cells secreted HER3 ligand HRG (Yonesaka, 2011), and expressed 17000 HER3 receptors per cell. At day 31 post-implantation (corresponding to 20 days after the beginning of the treatment), anti-HER3 mAbs inhibited significantly tumor growth by approximately 53±6% in mice xenografted with A431 cancer cells, compared with vehicle control (FIG. 16A; $p<0.001$). 16D3-C1 and 9F7-F11 mAbs delayed 50%-mean survival time for 21 days, with one out of eight treated mice being cured in each group at the end of the experiment (120 days) (FIG. 16B).

As shown in FIG. 17A, we observed a significant 68±4%-reduction in pancreatic BxPC3 tumor growth in antibody-treated mice at day 56 post-tumor implantation (corresponding to 26 days after the beginning of antibody treatment), with regard to tumor size measured in mice treated with vehicle ($p<0.001$). At the end of the experiment (135 days), Kaplan-Meier analysis revealed an 18-day delay in 50%-mean survival time for pancreatic BxPC3-xenografted mice treated with anti-HER3 muAb 9F7-F11 (FIG. 17B). In add, HER3-specific mAb 16D3-C1 induced a more prolonged 24-day delay in survival time of mice xenografted with HER2-non amplified/PIK3CA-wt BxPC3 pancreatic tumor cells, with one out of eight mice being completely cured. In this case (FIG. 18), tumors extracted from 16D3-C1-treated mice demonstrated an inhibition of Y1289 HER3 phosphorylation and a downregulation of the HER3 receptor, with regard to tumors extracted from vehicle-treated mice. Taken together, these results demonstrated that mAbs 16D3-C1 and 9F7-F11 could be efficient in tumors independently of HRG addiction or p53 mutation status.

We previously demonstrated that combination of therapeutic antibody trastuzumab with other targeted therapies demonstrated a synergistic effect on carcinomas with low HER2 expression (Larbouret, 2007, 2010). To check the in vivo effects of HER3-specific antibodies as dual agents with anti-HER2 trastuzumab (Tz) on carcinomas with low HER2 expression, we xenografted mice with HER2$^{low}$ epidermoid A431 and lung A549 cancer cells, which secreted HRG (Yonesaka, 2011; Zhou, 2006), and showed no (Farhan, 2006) to moderate effect (Nakamura, 2005) to trastuzumab therapy, respectively. To discriminate a potential synergistic effect, sub-efficient dose of anti-HER3 muAb 16D3-C1 combined with trastuzumab was administered at only 10 mg/kg every 3 days for 4 weeks (Q3d-4W). As shown in FIG. 19A, a 60%-regression in A431 tumor growth was significantly observed in mice treated with dual combination of 16D3-C1 and Tz ($p<0.001$) at day 35 post-tumor implantation, with regard to a 25%-reduction in tumor size of 16D3-C1-treated mice and no effect observed in xenografted mice treated with trastuzumab alone or vehicle. Similarly, significant 75%-greater regression in tumor growth in A549-xenografted mice treated with dual combination 16D3-C1+Tz was measured ($p<0.001$) in comparison to those observed in mice treated with antibodies alone (50%). Taken together, these results demonstrated that dual combination of HER3-specific antibody and anti-HER2 antibody could be efficient on HER2$^{low}$ carcinomas not eligible for trastuzumab therapy.

REFERENCES

Throughout this application, various references describe the state of the art to which this invention pertains. The disclosures of these references are hereby incorporated by reference into the present disclosure.

The invention claimed is:

1. An isolated monoclonal antibody that specifically binds to the extracellular domain of HER-3 produced by or obtainable from a hybridoma deposited as CNCM-I-4486 or that competes for binding to the extracellular domain of human HER-3 with the antibody being produced by or obtainable from a hybridoma deposited as CNCM-I-4486.

2. The isolated monoclonal antibody according to claim 1 wherein said antibody is selected from the group consisting of a murine antibody, a chimeric antibody, a humanized antibody, and a human antibody.

3. The isolated monoclonal antibody according to claim 1 which comprises a variable light chain (VL) comprising the CDRs of the VL chain of the antibody obtainable from hybridoma deposited as CNCM-I-4486 and a variable heavy chain (VH) comprising the CDRs of the VH chain of the antibody obtainable from hybridoma deposited as CNCM-I-4486.

4. The isolated monoclonal antibody according to claim 3 which comprises the VL chain of the antibody obtainable from hybridoma deposited as CNCM-I-4486 and the VH chain of the antibody obtainable from hybridoma deposited as CNCM-I-4486.

5. The isolated monoclonal antibody according to claim 4 which is a monoclonal chimeric antibody, and which comprises the variable domains of the antibody obtainable from hybridoma deposited as CNCM-I-4486.

6. The isolated monoclonal antibody according to claim 3 which is a monoclonal humanized antibody comprising the CDRs of the antibody obtainable from hybridoma deposited as CNCM-I-4486.

7. The isolated monoclonal antibody according to claim 3 which is the murine monoclonal antibody (16D3-C1) obtainable from the hybridoma available under CNCM deposit number I-4486.

8. An antibody fragment of an isolated monoclonal antibody that specifically binds to the extracellular domain of HER-3 produced by or obtainable from a hybridoma deposited as CNCM-I-4486 or of an isolated monoclonal antibody that competes for binding to the extracellular domain of human HER-3 with the antibody being produced by or obtainable from a hybridoma deposited as CNCM-I-4486, wherein said antibody fragment is selected from the group consisting of Fv, Fab, F(ab')2, Fab', dsFv, scFv, sc(Fv)2 and diabodies.

9. A nucleic acid encoding the VH domain or the VL domain of an isolated monoclonal antibody that specifically binds to the extracellular domain of HER-3 produced by or obtainable from the hybridoma deposited as CNCM-I-4486 or the VH domain or the VL domain of an isolated monoclonal antibody that competes for binding to the extracellular domain of human HER-3 with the antibody being produced by or obtainable from a hybridoma deposited as CNCM-I-4486.

10. A vector comprising a nucleic acid encoding the VH domain or the VL domain of an isolated monoclonal antibody that specifically binds to the extracellular domain of HER-3 produced by or obtainable from the hybridoma deposited as CNCM-I-4486 or a nucleic acid encoding the VH domain or the VL domain of an isolated monoclonal antibody that competes for binding to the extracellular domain of human HER-3 with the antibody being produced by or obtainable from a hybridoma deposited as CNCM-I-4486.

11. A host cell which has been transfected, infected or transformed by
a first nucleic acid encoding the VH domain or the VL domain of an isolated monoclonal antibody that specifically binds to the extracellular domain of HER-3 produced by or obtainable from the hybridoma deposited as CNCM-I-4486; or
a second nucleic acid encoding the VH domain or the VL domain of an isolated monoclonal antibody that competes for binding to the extracellular domain of human HER-3 with the antibody being produced by or obtainable from a hybridoma deposited as CNCM-I-4486; or
a vector comprising said first or second nucleic acid.

12. A pharmaceutical composition comprising an isolated monoclonal antibody that specifically binds to the extracellular domain of HER-3 produced by or obtainable from the hybridoma deposited as CNCM-I-4486 or an isolated monoclonal antibody that competes for binding to the extracellular domain of human HER-3 with the antibody being produced by or obtainable from a hybridoma deposited as CNCM-I-4486.

13. A method of treating cancers that express HER-3 in a patient in need thereof, comprising
administering to said patient a therapeutically effective amount of an isolated monoclonal antibody that specifically binds to the extracellular domain of HER-3 produced by or obtainable from the hybridoma deposited as CNCM-I-4486 or an isolated monoclonal antibody that competes for binding to the extracellular domain of human HER-3 with the antibody being produced by or obtainable from a hybridoma deposited as CNCM-I-4486.

* * * * *